(12) United States Patent
Aboytes et al.

(10) Patent No.: US 9,855,052 B2
(45) Date of Patent: Jan. 2, 2018

(54) DEVICES AND METHODS FOR THE TREATMENT OF VASCULAR DEFECTS

(71) Applicant: Covidien LP, Mansfield, MA (US)

(72) Inventors: Maria Aboytes, Palo Alto, CA (US); Arturo S. Rosqueta, San Jose, CA (US)

(73) Assignee: Covidien LP, Mansfield, MA (US)

( * ) Notice: Subject to any disclaimer, the term of this patent is extended or adjusted under 35 U.S.C. 154(b) by 314 days.

(21) Appl. No.: 14/603,998

(22) Filed: Jan. 23, 2015

(65) Prior Publication Data

US 2015/0209050 A1 Jul. 30, 2015

Related U.S. Application Data

(63) Continuation of application No. 13/230,628, filed on Sep. 12, 2011, now Pat. No. 8,974,512.

(Continued)

(51) Int. Cl.
*A61F 2/06* (2013.01)
*A61B 17/12* (2006.01)
(Continued)

(52) U.S. Cl.
CPC .. *A61B 17/12172* (2013.01); *A61B 17/00234* (2013.01); *A61B 17/1214* (2013.01);
(Continued)

(58) Field of Classification Search
CPC ........ A61B 17/12031; A61B 17/12113; A61B 17/1214; A61B 17/12145;
(Continued)

(56) References Cited

U.S. PATENT DOCUMENTS 5,250,071 A 10/1993 Palermo
5,645,558 A 7/1997 Horton et al.
(Continued)

FOREIGN PATENT DOCUMENTS

CA 2812012 3/2012
CA 2812012 A1 3/2012
(Continued)

OTHER PUBLICATIONS

Extended European Search Report dated Jan. 7, 2015 in European Patent Application No. 11824250.2, 7 pages.
(Continued)

*Primary Examiner* — Robert Lynch
(74) *Attorney, Agent, or Firm* — FORTEM IP LLP; Mary Fox

(57) ABSTRACT

Devices and methods for treating vascular defects, such as, for example, balloon-type aneurysms, are described herein. In one embodiment, an apparatus includes an insertion portion and an expandable implant. The expandable implant is configured to be deployed in an aneurysm and is coupled to the insertion portion. The expandable implant has a first portion and a second portion coupled to the first portion. The expandable implant is movable between a first configuration in which the first portion and the second portion are substantially linearly aligned and a second configuration in which the second portion at least partially overlaps the first portion.

10 Claims, 10 Drawing Sheets

Related U.S. Application Data

(60) Provisional application No. 61/381,770, filed on Sep. 10, 2010.

(51) Int. Cl.
*A61B 17/00* (2006.01)
*A61B 90/00* (2016.01)

(52) U.S. Cl.
CPC .... *A61B 17/1215* (2013.01); *A61B 17/12031* (2013.01); *A61B 17/12113* (2013.01); *A61B 17/12145* (2013.01); *A61B 17/12163* (2013.01); *A61B 17/12168* (2013.01); *A61B 90/39* (2016.02); *A61B 2017/1205* (2013.01); *A61B 2017/12054* (2013.01); *A61B 2090/3966* (2016.02)

(58) Field of Classification Search
CPC ........ A61B 17/12168; A61B 17/12172; A61B 2017/1205; A61B 2017/12054
See application file for complete search history.

(56) References Cited

U.S. PATENT DOCUMENTS

| | | | |
|---|---|---|---|
| 5,725,552 A | 3/1998 | Kotula et al. |
| 5,733,294 A | 3/1998 | Forber et al. |
| 5,741,333 A | 4/1998 | Frid et al. |
| 5,749,891 A | 5/1998 | Ken et al. |
| 5,749,919 A | 5/1998 | Blanc |
| 5,814,062 A | 9/1998 | Sepetka et al. |
| 5,911,731 A | 6/1999 | Pham et al. |
| 5,916,235 A | 6/1999 | Guglielmi |
| 5,925,060 A | 7/1999 | Forber |
| 5,928,260 A | 7/1999 | Chin et al. |
| 5,935,148 A | 8/1999 | Villar et al. |
| 5,944,738 A | 8/1999 | Amplatz et al. |
| 5,951,599 A | 9/1999 | McCrory |
| 5,964,797 A | 10/1999 | Ho |
| 5,976,169 A | 11/1999 | Imran et al. |
| 5,980,554 A | 11/1999 | Lenker et al. |
| 6,022,374 A | 2/2000 | Imran |
| 6,033,423 A | 3/2000 | Ken et al. |
| 6,036,720 A | 3/2000 | Abrams et al. |
| 6,063,070 A | 5/2000 | Eder |
| 6,063,104 A | 5/2000 | Villar et al. |
| 6,086,577 A | 7/2000 | Ken et al. |
| 6,090,125 A | 7/2000 | Horton |
| 6,093,199 A | 7/2000 | Brown et al. |
| 6,096,021 A | 8/2000 | Helm et al. |
| 6,123,715 A | 9/2000 | Amplatz et al. |
| 6,139,564 A | 10/2000 | Teoh |
| 6,152,144 A | 11/2000 | Lesh et al. |
| 6,159,531 A | 12/2000 | Dang et al. |
| 6,168,615 B1 | 1/2001 | Ken et al. |
| 6,168,622 B1 | 1/2001 | Mazzocchi |
| 6,344,048 B1 | 2/2002 | Chin et al. |
| 6,346,117 B1 | 2/2002 | Greenhalgh |
| 6,350,270 B1 | 2/2002 | Roue |
| 6,368,339 B1 | 4/2002 | Amplatz et al. |
| 6,371,980 B1 | 4/2002 | Rudakov et al. |
| 6,375,668 B1 | 4/2002 | Gifford et al. |
| 6,383,174 B1 | 5/2002 | Eder |
| 6,391,037 B1 | 5/2002 | Greenhalgh |
| 6,428,558 B1 | 8/2002 | Jones et al. |
| 6,447,531 B1 | 9/2002 | Amplatz |
| 6,451,050 B1 | 9/2002 | Rudakov et al. |
| 6,454,780 B1 | 9/2002 | Wallace |
| 6,494,884 B2 | 12/2002 | Gifford, III et al. |
| 6,506,204 B2 | 1/2003 | Mazzocchi |
| 6,511,468 B1 | 1/2003 | Cragg et al. |
| 6,547,804 B2 | 4/2003 | Porter et al. |
| 6,551,303 B1 | 4/2003 | Van Tassel et al. |
| 6,579,303 B2 | 6/2003 | Amplatz |
| 6,585,748 B1 | 7/2003 | Jeffree |
| 6,589,256 B2 | 7/2003 | Forber |
| 6,589,265 B1 | 7/2003 | Palmer et al. |
| 6,599,308 B2 | 7/2003 | Amplatz |
| 6,605,102 B1 | 8/2003 | Mazzocchi et al. |
| 6,605,111 B2 | 8/2003 | Bose et al. |
| 6,613,074 B1 | 9/2003 | Mitelberg et al. |
| 6,626,939 B1 | 9/2003 | Burnside et al. |
| 6,635,068 B1 | 10/2003 | Dubrul et al. |
| 6,652,556 B1 | 11/2003 | VanTassel et al. |
| 6,666,882 B1 | 12/2003 | Bose et al. |
| 6,669,721 B1 | 12/2003 | Bose et al. |
| 6,682,546 B2 | 1/2004 | Amplatz |
| 6,689,486 B2 | 2/2004 | Ho et al. |
| 6,730,108 B2 | 5/2004 | Van Tassel et al. |
| 6,746,468 B1 | 6/2004 | Sepetka |
| 6,746,890 B2 | 6/2004 | Gupta et al. |
| 6,780,196 B2 | 8/2004 | Chin et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,905,503 B2 | 6/2005 | Gifford et al. |
| 6,936,055 B1 | 8/2005 | Ken et al. |
| 6,991,617 B2 | 1/2006 | Hektner et al. |
| 6,994,092 B2 | 2/2006 | Van Der Burg et al. |
| 6,994,717 B2 | 2/2006 | Kónya et al. |
| 7,011,671 B2 | 3/2006 | Welch |
| 7,029,487 B2 | 4/2006 | Green, Jr. et al. |
| 7,083,632 B2 | 8/2006 | Avellanet et al. |
| 7,128,073 B1 | 10/2006 | Van Der Burg et al. |
| 7,128,736 B1 | 10/2006 | Abrams et al. |
| 7,169,177 B2 | 1/2007 | Obara |
| 7,195,636 B2 | 3/2007 | Avellanet et al. |
| 7,229,461 B2 | 6/2007 | Chin et al. |
| 7,232,461 B2 | 6/2007 | Ramer |
| 7,326,225 B2 | 2/2008 | Ferrera et al. |
| 7,331,980 B2 | 2/2008 | Dubrul et al. |
| 7,419,503 B2 | 9/2008 | Pulnev et al. |
| 7,597,704 B2 | 10/2009 | Frazier et al. |
| 7,708,754 B2 | 5/2010 | Balgobin et al. |
| 8,142,456 B2 | 3/2012 | Rosqueta et al. |
| 8,211,160 B2 | 7/2012 | Garrison et al. |
| 8,333,783 B2 | 12/2012 | Braun et al. |
| 8,343,167 B2 | 1/2013 | Henson |
| 8,361,104 B2 | 1/2013 | Jones et al. |
| 8,361,138 B2 | 1/2013 | Adams |
| 8,834,515 B2 | 9/2014 | Win et al. |
| 8,974,512 B2 | 3/2015 | Aboytes et al. |
| 8,998,947 B2 | 4/2015 | Aboytes et al. |
| 2002/0062145 A1 | 5/2002 | Rudakov et al. |
| 2002/0169473 A1 | 11/2002 | Sepetka et al. |
| 2002/0193812 A1 | 12/2002 | Patel et al. |
| 2002/0193813 A1 | 12/2002 | Helkowski et al. |
| 2003/0004533 A1 | 1/2003 | Dieck et al. |
| 2003/0004568 A1 | 1/2003 | Ken et al. |
| 2003/0028209 A1 | 2/2003 | Teoh et al. |
| 2003/0055440 A1 | 3/2003 | Jones et al. |
| 2003/0093111 A1 | 5/2003 | Ken et al. |
| 2003/0113478 A1 | 6/2003 | Dang et al. |
| 2003/0114918 A1 | 6/2003 | Garrison et al. |
| 2004/0064093 A1 | 4/2004 | Hektner et al. |
| 2004/0115164 A1 | 6/2004 | Pierce et al. |
| 2004/0161451 A1 | 8/2004 | Pierce et al. |
| 2004/0172056 A1 | 9/2004 | Guterman et al. |
| 2005/0085836 A1 | 4/2005 | Raymond |
| 2005/0222580 A1 | 10/2005 | Gifford et al. |
| 2005/0277978 A1 | 12/2005 | Greenhalgh |
| 2006/0052816 A1 | 3/2006 | Bates et al. |
| 2006/0064151 A1 | 3/2006 | Guterman et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0116714 A1 | 6/2006 | Sepetka et al. |
| 2006/0155323 A1 | 7/2006 | Porter et al. |
| 2006/0190070 A1 | 8/2006 | Dieck et al. |
| 2006/0206140 A1 | 9/2006 | Shaolian et al. |
| 2006/0206198 A1 | 9/2006 | Churchwell et al. |
| 2006/0206199 A1 | 9/2006 | Churchwell et al. |
| 2006/0241686 A1 | 10/2006 | Ferrera et al. |

(56) References Cited

U.S. PATENT DOCUMENTS

| | | |
|---|---|---|
| 2006/0247680 A1 | 11/2006 | Amplatz et al. |
| 2006/0271162 A1 | 11/2006 | Vito et al. |
| 2007/0010850 A1 | 1/2007 | Balgobin et al. |
| 2007/0083226 A1 | 4/2007 | Buiser et al. |
| 2007/0167876 A1 | 7/2007 | Euteneuer et al. |
| 2007/0167877 A1 | 7/2007 | Euteneuer et al. |
| 2007/0167972 A1 | 7/2007 | Euteneuer et al. |
| 2007/0179520 A1 | 8/2007 | West |
| 2007/0185442 A1 | 8/2007 | Euteneuer et al. |
| 2007/0185443 A1 | 8/2007 | Euteneuer et al. |
| 2007/0185444 A1 | 8/2007 | Euteneuer et al. |
| 2007/0185457 A1 | 8/2007 | Euteneuer et al. |
| 2007/0219619 A1 | 9/2007 | Dieck et al. |
| 2007/0276426 A1 | 11/2007 | Euteneuer |
| 2007/0276427 A1 | 11/2007 | Euteneuer |
| 2007/0282373 A1 | 12/2007 | Ashby et al. |
| 2007/0288083 A1 | 12/2007 | Hines |
| 2008/0082176 A1 | 4/2008 | Slazas |
| 2008/0114391 A1 | 5/2008 | Dieck et al. |
| 2008/0114436 A1 | 5/2008 | Dieck et al. |
| 2008/0200945 A1* | 8/2008 | Amplatz ............ A61B 17/0057 606/195 |
| 2008/0200979 A1 | 8/2008 | Dieck et al. |
| 2008/0221600 A1 | 9/2008 | Dieck et al. |
| 2008/0281350 A1 | 11/2008 | Sepetka et al. |
| 2009/0043375 A1 | 2/2009 | Rudakov et al. |
| 2009/0062899 A1 | 3/2009 | Dang et al. |
| 2009/0187214 A1 | 7/2009 | Amplatz et al. |
| 2009/0264978 A1 | 10/2009 | Dieck et al. |
| 2009/0275974 A1 | 11/2009 | Marchand et al. |
| 2009/0287291 A1 | 11/2009 | Becking et al. |
| 2009/0287292 A1 | 11/2009 | Becking et al. |
| 2009/0287294 A1 | 11/2009 | Rosqueta et al. |
| 2009/0318892 A1 | 12/2009 | Aboytes et al. |
| 2009/0318941 A1 | 12/2009 | Sepetka et al. |
| 2009/0319023 A1 | 12/2009 | Hildebrand et al. |
| 2010/0030200 A1 | 2/2010 | Strauss et al. |
| 2010/0036410 A1 | 2/2010 | Krolik et al. |
| 2010/0139465 A1 | 6/2010 | Christian et al. |
| 2010/0174269 A1 | 7/2010 | Tompkins et al. |
| 2010/0185271 A1 | 7/2010 | Zhang |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0262014 A1 | 10/2010 | Huang |
| 2010/0268201 A1 | 10/2010 | Tieu et al. |
| 2011/0022149 A1 | 1/2011 | Cox et al. |
| 2011/0046658 A1 | 2/2011 | Connor et al. |
| 2011/0077620 A1 | 3/2011 | Debeer |
| 2011/0137332 A1 | 6/2011 | Sepetka et al. |
| 2011/0144669 A1 | 6/2011 | Becking et al. |
| 2011/0152993 A1* | 6/2011 | Marchand ........ A61B 17/12022 623/1.2 |
| 2011/0202085 A1 | 8/2011 | Loganathan et al. |
| 2011/0208227 A1 | 8/2011 | Becking |
| 2011/0224776 A1 | 9/2011 | Sepetka et al. |
| 2011/0265943 A1 | 11/2011 | Rosqueta et al. |
| 2011/0319926 A1 | 12/2011 | Becking et al. |
| 2012/0022572 A1 | 1/2012 | Braun et al. |
| 2012/0041472 A1 | 2/2012 | Tan et al. |
| 2012/0101510 A1 | 4/2012 | Lenker et al. |
| 2012/0116350 A1 | 5/2012 | Strauss et al. |
| 2012/0165919 A1 | 6/2012 | Cox et al. |
| 2012/0197283 A1 | 8/2012 | Marchand et al. |
| 2012/0239074 A1 | 9/2012 | Aboytes et al. |
| 2012/0283769 A1 | 11/2012 | Cruise et al. |
| 2012/0316598 A1 | 12/2012 | Becking et al. |
| 2012/0330341 A1 | 12/2012 | Becking et al. |
| 2012/0330347 A1 | 12/2012 | Becking et al. |
| 2012/0330348 A1 | 12/2012 | Strauss et al. |
| 2013/0066357 A1 | 3/2013 | Aboytes et al. |
| 2013/0066360 A1 | 3/2013 | Becking et al. |
| 2013/0085522 A1 | 4/2013 | Becking et al. |
| 2013/0116722 A1 | 5/2013 | Aboytes et al. |
| 2015/0272590 A1 | 10/2015 | Aboytes et al. |
| 2015/0342613 A1 | 12/2015 | Aboytes et al. |
| 2016/0262766 A1 | 9/2016 | Aboytes et al. |

FOREIGN PATENT DOCUMENTS

| | | |
|---|---|---|
| DE | 102011102933 | 12/2012 |
| EP | 0717969 | 6/1996 |
| EP | 1813213 | 8/2007 |
| EP | 2208483 | 7/2010 |
| EP | 2208483 A1 | 7/2010 |
| EP | 2609888 | 7/2013 |
| ER | 2890306 | 3/2007 |
| JP | 2005261951 | 9/2005 |
| JP | 2008521492 | 6/2008 |
| JP | 2010523260 T | 7/2010 |
| WO | 9406502 | 3/1994 |
| WO | 9409705 | 5/1994 |
| WO | 9907294 | 2/1999 |
| WO | 9929260 | 6/1999 |
| WO | 02054980 | 7/2002 |
| WO | 02089863 | 11/2002 |
| WO | 2005099634 | 10/2005 |
| WO | 2006034149 | 3/2006 |
| WO | 2007121405 | 10/2007 |
| WO | 2008074027 | 6/2008 |
| WO | 2009044528 A1 | 1/2009 |
| WO | 2010009019 | 1/2010 |
| WO | 2010027363 | 3/2010 |
| WO | 2010077599 A1 | 7/2010 |
| WO | 2011095966 | 3/2011 |
| WO | 2012034135 A1 | 3/2012 |
| WO | 2013112944 | 8/2013 |
| WO | 2013138615 A2 | 9/2013 |

OTHER PUBLICATIONS

Extended European Search Report dated Jul. 1, 2016 in European Patent Application No. 13867906.3; 9 pages.

Extended European Search Report dated Mar. 2, 2016 in European Patent Application No. 137616710.0; 13 pages.

Extended European Search Report dated Jan. 30, 2017 in European Patent Application No. 16190494.1; 9 pages.

International Search Report and Written Opinion for Application No. PCT/US2011/051268; Applicant: Maria Aboytes; dated Jan. 3, 2012 (10 pages).

International Search Report and Written Opinion for Application No. PCT/US2013/031466; Applicant: Medina Medical, Inc.; dated Jun. 25, 2014 (11 pages).

International Search Report and Written Opinion for Application No. PCT/US2013/077767; Applicant: Medina Medical, Inc.; dated Mar. 19, 2014 (9 pages).

* cited by examiner

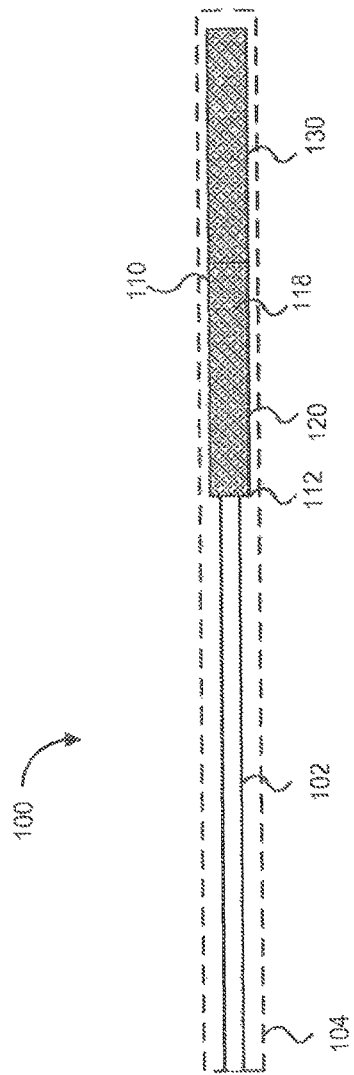
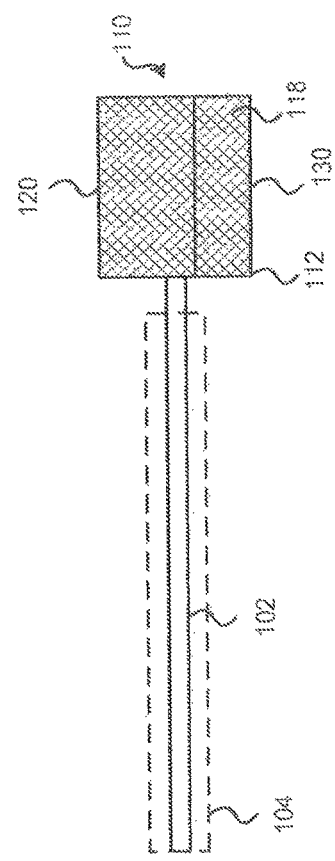

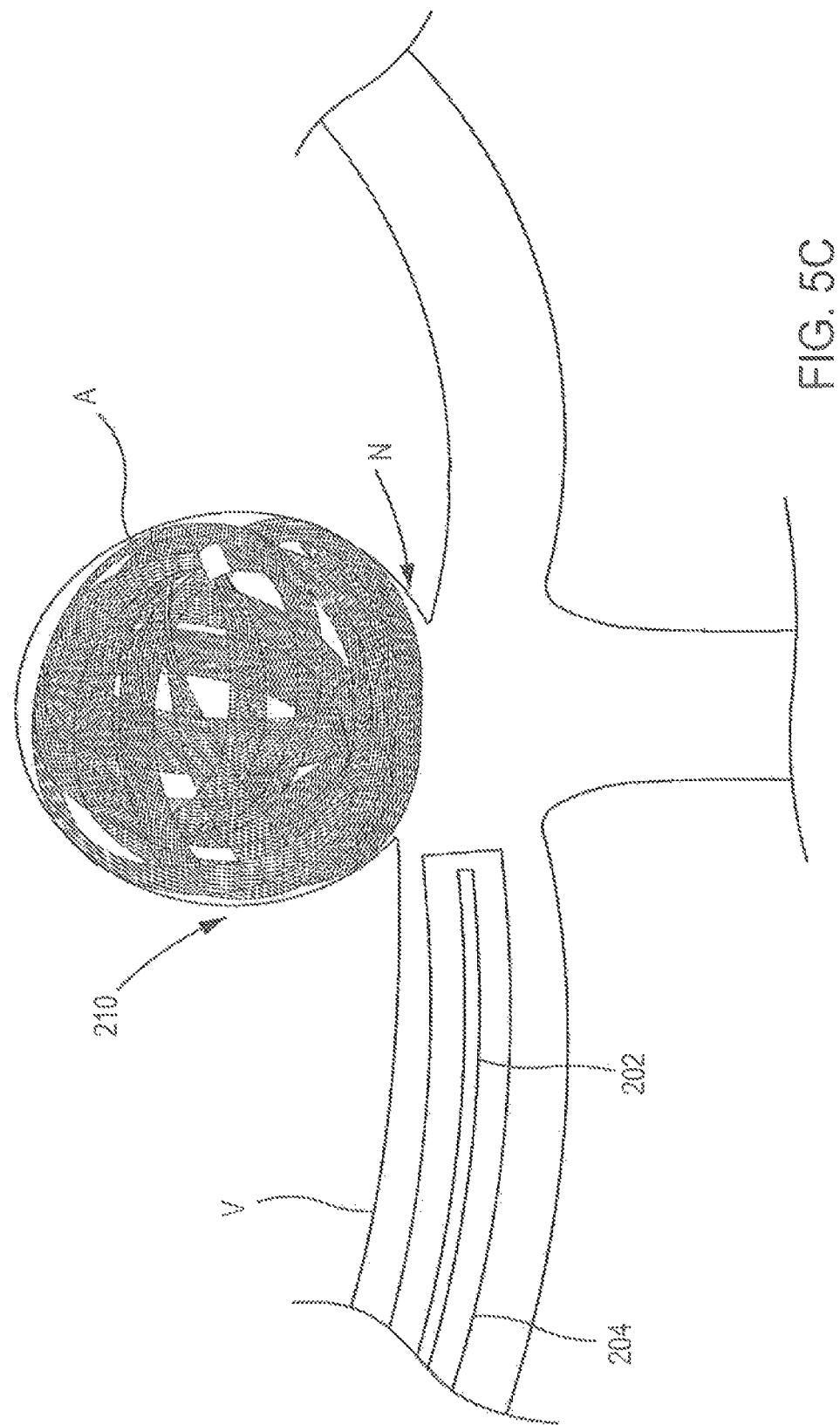

DEVICES AND METHODS FOR THE TREATMENT OF VASCULAR DEFECTS

CROSS-REFERENCE TO RELATED APPLICATION(S)

This application is a divisional of U.S. Pat. No. 8,974,512, entitled "Devices and Methods for the Treatment of Vascular Defects," file Sep. 12, 2011, which claims priority to and the benefit of U.S. Provisional Patent Application No. 61/381,770, entitled "Electropositive Neurovascular Endothelialization Device," filed Sep. 10, 2010, both disclosures of which are hereby incorporated by reference herein in their entireties.

BACKGROUND

The invention relates generally to medical devices and more particularly to expandable medical devices and methods for treating vascular defects. For example, the invention can relate to expandable medical devices and methods for treating an aneurysm. Aneurysms are dilations in a blood vessel caused from weakening of a blood vessel wall. The dilation is produced by the pressure exerted by normal blood flow, which can cause the weakened segment of the blood vessel to swell. In some cases, this swelling results in a sac, or balloon-like polyp protruding from the main or parent vessel. Continued growth and/or eventual rupture of the ballooned arterial wall can have devastating results for a patient. As such, unruptured aneurysms should be treated to prevent hemorrhage. Additionally, ruptured aneurysms can be treated to avert a subsequent rupture and/or additional damage.

Some known medical devices and treatment methods used for treating an aneurysm include delivering a platinum coil to the sac of the aneurysm. The platinum coil is electrolytically separated from a delivery wire, thus inducing a charge in the coil which can cause a thrombotic effect in the aneurysm. In known procedures, about 30% of the volume of the aneurysm is packed with coils. Such known devices and methods, however, often have an about 30% recanalization rate, meaning blood flow returns to the aneurysm again and can cause the coil-packed aneurysm to swell further. Additionally, such known devices and methods require prolonged procedure times for the patient and correspondingly increased exposure to radiation for the patient. Moreover, such devices and methods do not treat the neck of the aneurysm, which is the area between the parent blood vessel and the sac of the aneurysm.

Another known treatment method includes the use of both a coil and a stent. The coil is delivered to the sac of the aneurysm as described above, and the stent is positioned within the parent blood vessel such that a portion of the stent is disposed over the neck of the aneurysm. Such procedures have several drawbacks. For one, delivery of two separate types of devices (i.e., coil(s) and a stent) is a more complex procedure, often resulting in a longer procedure time for the patient. The stent may lead to intra-stent stenosis of the blood vessel. Additionally, a patient would likely be required to take a blood thinner indefinitely following the procedure. Moreover, such devices and methods are not suitable for treatment of aneurysms positioned at a bifurcation of the blood vessel (i.e., between adjacent branches of a vessel).

Another known device and treatment method includes the use of a flow diverter delivered to the parent blood vessel adjacent the neck of the aneurysm. Generally, the flow diverter is positioned within the parent blood vessel over the neck of the aneurysm to prevent additional blood flow into the aneurysm from the vessel. In current procedures, more than one flow diverter is required per aneurysm to ensure blood flow is appropriately diverted from the aneurysm. Such a device and treatment method has similar drawbacks to the use of a stent, described above. Specifically, the flow diverter may lead to stenosis of the blood vessel and the patient would likely be required to take a blood thinner indefinitely following the procedure. Additionally, known flow diverters are not suitable for treating an aneurysm positioned at a bifurcation of the blood vessel. Moreover, long term follow-up of patients treated using a flow diverter is showing an increased rate of recanalization to the aneurysm.

Thus, there is a need for improved systems, devices and methods for treating vascular defects, such as balloon-type aneurysms, as described herein.

SUMMARY

Devices and methods for treating vascular defects, such as, for example, balloon type aneurysms, are described herein. In one embodiment, an apparatus includes an insertion portion and an expandable implant. The expandable implant is configured to be deployed in an aneurysm and is coupled to the insertion portion. The expandable implant has a first portion and a second portion coupled to the first portion. The expandable implant is movable between a first configuration in which the first portion and the second portion are substantially linearly aligned and a second configuration in which the second portion at least partially overlaps the first portion.

BRIEF DESCRIPTION OF THE DRAWINGS

FIG. 1 is a schematic illustration of a medical device according to an embodiment in a first configuration.

FIG. 2 is a schematic illustration of a medical device according to an embodiment in a second configuration.

FIG. 5C is a view of the medical device of FIG. 3 in a third configuration during insertion into an aneurysm.

DETAILED DESCRIPTION

Figure 3:
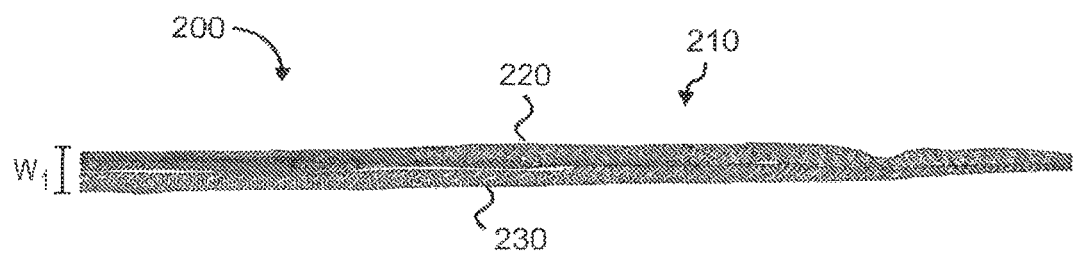
FIG. 3 is a side view of a medical device according to an embodiment in a first configuration.

Medical devices and methods of treatment are described herein to treat patients experiencing a vascular defect, such as an aneurysm, in a circulatory blood vessel and the effects of that defect, including hemorrhagic stroke. For example, the devices and methods described herein can be useful for treating vascular defects present in vasculature that is tortuous, of small-diameter, and/or that is otherwise difficult to access. More specifically, the devices and methods described herein can be useful for treating saccular (also referred to as balloon-type or berry) aneurysms, bifurcation aneurysms, fistulas, and other defects in vasculature, including defects in neurovasculature. The medical devices and methods of treatment described herein can reduce hemorrhagic events while promoting endothelialization of an opening between an aneurysm and a parent blood vessel from which the aneurysm bulge formed (e.g., at a neck of the aneurysm).

Various embodiments of a medical device for occupying all or substantially all of the volume of an aneurysm and/or promoting endothelialization at or proximate to the aneurysm are described herein. In some embodiments, the medical device includes an expandable implant including an electropositive woven or braided material. The filaments or strands forming the braid or weave are configured to encourage recruitment and/or retention of endothelial cells to the device and therefore within the defect. The expandable implant is configured to assume a non-linear predetermined three-dimensional shape within a sac of the aneurysm upon release from a tubular or other delivery constraint (e.g., a catheter or cannula). The electropositive woven or braided material has a particular porosity and includes multiple openings between the filaments or strands when the expandable implant is in the expanded configuration. Such openings are ideal in the blood environment for harboring endothelial cells recruited to the site. The electropositivity of the material encourages endothelialization in the presence of the electronegative charges of the blood and body tissues. Said another way, the electropositivity of the expandable implant in relation to a charge of blood and tissue (which is electronegative in comparison) provides an environment in the defect that promotes endothelialization. Endothelialization within the defect can ultimately result in the defect walling-off from the parent vessel. For example, the growth and development of an endothelial layer over a neck of an aneurysm can wall off the aneurysm from the parent vessel and allow flow dynamics to equilibrate at the defect. As such, the device can be configured to facilitate healing the defect and preventing recanalization because tissue is created from within the body that resists aberrant blood flow and redistributes the flow pressure that may have created the defect. Upon healing with endothelialization, the pressure is evenly distributed along the parent vessel in a manner that precludes recanalization at the defect post-treatment. Furthermore, blood from within the parent vessel no longer has access to the walled off defect once the endothelialization process is complete. Additionally, at least a portion of the expandable implant can be positioned over the neck of the aneurysm once the implant is deployed within the aneurysm such that the portion disrupts the flow of blood from the parent vessel into the aneurysm. As such, the expandable implant provides blood flow disruption in advance of and in addition to growth and development of the endothelial layer over the neck of the aneurysm.

A medical device described herein can include an insertion portion (e.g., a guide wire) and an expandable implant formed with, for example, woven or braided filaments in a mesh-like configuration. The terms mesh and braid can each refer herein to a fabric or material of woven or braided filaments or strands of wire or polymer. The expandable implant of the medical device can be configured to compress or collapse for delivery into a blood vessel. In some embodiments, the medical device can be inserted while in a collapsed or compressed configuration through a delivery device, such as, for example, a microcatheter, cannula, delivery tube or sheath. In some embodiments, the medical device can be deployed without the use of such a delivery device.

The expandable implant of the medical device can have a collapsed or compressed configuration such that the expandable implant has a diameter that can fit within the narrow constraints of the neurovasculature and/or within a lumen of a delivery catheter. The expandable implant of the medical device can be formed with, for example, an arrangement of strands (e.g., a mesh or braid arrangement of strands or filaments) that can compress and expand. Such materials include Nitinol, MP35N, stainless steel, cobalt chromium, titanium, platinum, tantalum, tungsten, or alloys thereof, or polyester, polyethylene (PET), Dacron, PEEK, vectron, and suture materials, and are available from Fort Wayne Metals of Fort Wayne, Ind., California Fine Wire Company of Grover Reach, Calif., other metal manufacturers, Ethicon Inc. of Somerville, N.J., Genzyme of Cambridge, Mass., Poly-Med, Inc. of Anderson, S.C., and/or other medical grade suture and fiber manufacturers. The expandable implant can be compressed over and/or along the insertion portion of the medical device. The insertion portion can be, for example, a wire. In some embodiments, a medical device includes an insertion portion movably disposable within a lumen of a delivery device. A distal portion of the insertion portion can be coupled to the expandable implant. The expandable implant can be moved from a collapsed configuration to an expanded configuration while disposed within, or as it is being inserted into, a defect (e.g., an aneurysm).

In some embodiments, the expandable implant can be formed with filaments of superelastic or shape memory material (such as, e.g., nitinol) and the braid or mesh can be set in a predefined shape prior to attaching the expandable implant to the insertion portion of the medical device. In such an embodiment, when the expandable implant is deployed and expands, it assumes a biased predetermined shape. The predetermined shape can be a generic shape, such as that of a sphere, or can be a custom-made shape based on a shape of a target aneurysm within a patient. Suitable materials are described in more detail herein.

The medical devices described herein can include one or more expandable implants formed with a woven mesh or braid that has variably sized apertures (also referred to herein as "openings" or "pores"). Said another way, the devices are formed with a material that has a particular porosity or pore density. In some embodiments, an expandable implant can have sections of mesh or braid having variation in density of the filaments and may include portions or bands of densely spaced filaments (i.e., lower porosity) spaced by portions or bands that are less dense (i.e., higher porosity). The less dense braid portion can have larger openings in the braid, while the more dense braid portion can have smaller openings in the braid. Material (e.g., bodily tissue such as endothelial cells) can be encouraged to enter and/or attach to interstices of the mesh of the expandable implant. For example, the more dense braid portion can be used to encourage greater endothelial cell attachment and the less dense braid portion can be used to reduce the overall weight and or material to be implanted in the patient. The less dense sections can also direct the final shape of the expandable implant. For example, sections of less dense (more open) mesh or braid can direct the effects of expansion of the implant.

In some embodiments, a medical device can be delivered to a desired treatment site within a vasculature by inserting the medical device through a lumen of a delivery catheter (e.g., a microcatheter). The expandable medical device can be inserted through the delivery catheter in a collapsed or compressed configuration. The expandable implant of the expandable medical device can be moved out through a distal end of the delivery catheter at the treatment site (e.g., into a sac of an aneurysm) and moved to an expanded configuration. In some embodiments, the delivery catheter is used to compress or collapse the expandable implant. For example, the expandable implant can be formed with a biased expanded configuration and when it is placed within a lumen of a catheter it is compressed. When the expandable implant is moved outside of the catheter, it can assume its biased expanded configuration. In the expanded configuration, a first portion of the expandable implant substantially overlaps a second portion of the expandable implant. The first and second portions of the expandable implant can be discrete structures or can be portions of a unitary or monolithically constructed device.

A medical device, such as an expandable implant, described herein can include a first porous member and a second porous member coupled to the first porous member. Each of the first and second porous members include a first end and a second end. The first and second porous members each have a collapsed configuration for insertion through a blood vessel and an expanded configuration for occupying at least a portion of the volume defined by the sac of an aneurysm. In some embodiments, the first porous member is substantially elongate and has a greater width in its expanded configuration than in its collapsed configuration. The second porous member is substantially elongate and has a greater width in its expanded configuration than in its collapsed configuration. In some embodiments, the width of the first porous member is greater than the width of the second porous member, for example, when each of the first and second porous members are in their expanded configurations.

In some embodiments, the first porous member is configured to occupy a first volume in its collapsed configuration and a second, greater, volume in its expanded configuration. For example, the first porous member can have a substantially spherical, oblong, or other suitable shape in its expanded configuration that occupies a greater volume than the substantially elongate shape of the first porous member in its collapsed configuration. The second porous member can be configured to move or curve into a three dimensional configuration in the expanded configuration such that a first segment of the second porous member overlaps with a second segment of the second porous member. In its expanded configuration, the second porous member can define an interior region configured to receive the first porous member in its expanded configuration. For example, in some embodiments, the second porous member has a substantially spherical shape with an open interior region configured to receive the first porous member.

In some embodiments, a medical device, such as an expandable implant, described herein can include a first porous member and a second porous member. Each of the first and second porous members include a first end and a second end. The first and second porous members each have a collapsed configuration for insertion through a blood vessel and an expanded configuration for occupying at least a portion of the volume defined by a sac of an aneurysm. The first and second porous members are each substantially elongate in the collapsed configuration. In its expanded configuration, the first porous member has a three-dimensional shape including a first segment configured to overlap with a second segment and defining an interior region. The second porous member is configured to be disposed in the interior region of the first porous member when each of the first and second porous members are in their respective expanded configurations. In some embodiments, the second porous member can be formed integrally or monolithically with the first porous member. In some embodiments, the second porous member can be woven or braided using the same filaments that form the first porous member.

In some embodiments, the expandable implant is in the form of a braided tube that includes fibers of a superelastic shape memory alloy, or polymeric fibers. In some embodiments, the expandable implant can effect a shape deformation inducing a substantially spherical contour. In some embodiments, the expandable implant can effect a shape deformation inducing a helical contour. In some embodiments, the shape deformation can include inducing radial expansion and/or axial shortening.

The medical devices described herein can be used to occupy at least a portion of the volume defined by a sac of an aneurysm and/or to promote endothelialization of the neck of the aneurysm to inhibit or stop blood flow into the aneurysm, which can lead to, for example, hemorrhagic stroke. In some embodiments, wire or polymer filaments can be used to form a woven mesh or braided strands that can be expandable, and have apertures sized to promote endothelial cell attachment at the aneurysm.

It is noted that, as used in this written description and the appended claims, the singular forms "a," "an" and "the" include plural referents unless the context clearly dictates otherwise. Thus, for example, the term "a lumen" is intended to mean a single lumen or a combination of lumens. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted first inside a patient's body. Thus, for example, the end first inserted inside a patient's body would be the distal end of the medical device, while the end outside of or inserted later into a patient's body would be the proximal end of the medical device. Additionally, the terms "first," "second," "third," and so on, used to describe similarly identified elements are for purposes of clarity only, and are not meant to imply a priority or that such numerical identifier must be associated with that particular element in the claims.

FIGS. 1 and 2 are schematic illustrations of a vascular medical device 100 according to an embodiment in a first configuration and a second configuration, respectively. The medical device is configured to promote healing of an aneurysm. More specifically, at least a portion of the medical device is configured to occupy at least a portion of the volume defined by a sac of the aneurysm and, in some embodiments, at least a portion of the medical device is configured to promote endothelial cell attachment over a neck of the aneurysm. Once endothelialization over the aneurysm neck is complete, blood flow into the aneurysm sac from a parent blood vessel (i.e., the vessel on which the aneurysm formed) is prevented.

The medical device 100 can include an insertion portion 102 and an expandable implant 110. The insertion portion 102 is coupled to the expandable implant 110, such as, for example, at a proximal portion 112 of the expandable implant 110. In some embodiments, the insertion portion 102 is removably coupled to the expandable implant 110. In this manner, the insertion portion 102 can be separated from the expandable implant 110 following delivery of the expandable implant to the aneurysm and removed from a patient's vasculature. The insertion portion 102 can be, for example, a guide wire or a distal end portion of a wire. The medical device 100 can be used with a cannula or catheter 104 (shown in dashed lines in FIGS. 1 and 2) to, for example, deliver the expandable implant 110 to the aneurysm.

The expandable implant 110 is configured to be deployed in the aneurysm (e.g., in a sac of an aneurysm). The expandable implant 110 has a first portion 120 and a second portion 130. As shown in FIG. 1, the expandable implant 110 has a first configuration in which the first portion 120 and the second portion 130 are substantially linearly aligned. In its first configuration, the expandable implant 110 is configured for insertion through a blood vessel. The expandable implant 110 is also configured for insertion through a neck of the aneurysm when in its first configuration.

The expandable implant 110 is movable between its first configuration and a second configuration in which the second portion 130 at least partially overlaps the first portion 120, as shown in FIG. 2. For example, the second portion 130 can be configured to bend, curve and/or twist in multiple turns such that multiple segments of the first portion 120 and the second portion 130 are overlapped. Additionally, at least one of the first portion 120 and the second portion 130 can be configured to bend or curve in multiple turns such that the respective first or second portion is overlapped with itself. In some embodiments, the expandable implant 110 can be understood to have multiple first portions and multiple second portions. In other words, the expandable implant can continually overlap itself in its deployed configuration to occupy all or substantially all of the volume of the aneurysm.

In its second configuration, the expandable implant 110 is configured to occupy at least a portion of the volume defined by the sac of the aneurysm. In some embodiments, when the expandable implant 110 is in its second configuration, at least a portion of the expandable implant is configured to be positioned over the neck of the aneurysm. For example, the portion of the expandable implant 110 at which the second portion 130 overlaps the first portion 120 can be configured to be positioned over the neck of the aneurysm. As such, the portion of the expandable implant 110 disposed over the aneurysm neck has an increased density (e.g., a dual density compared to the first portion 120 or the second portion 130 individually), which helps to limit or prevent blood flow from entering the sac of the aneurysm. The portion of the expandable implant 110 positioned over the aneurysm neck can be a scaffold for endothelial cell attachment at the aneurysm neck. For example, the portion of the expandable implant 110 positionable over the aneurysm neck can be porous, such as by including a porous mesh, as described in more detail herein. In some embodiments, the first portion 120 and the second portion 130 of the expandable implant 110 are biased to the second configuration.

As noted above, in some embodiments, at least a portion of the expandable implant 110 is porous. For example, in some embodiments, at least a portion of the expandable implant 110 can include and/or be constructed of a mesh (e.g., woven, braided, or laser-cut) material such that a wall or layer of the expandable implant 110 defines multiple openings or interstices 118. More specifically, in some embodiments, at least one of or both the first portion 120 and the second portion 130 of the expandable implant 110 can include the porous mesh. The porous mesh can have a first porosity when the expandable implant 110 is in its first configuration and a second porosity when the expandable implant is in its second configuration. More specifically, in some embodiments, the porous mesh can have a greater porosity when the expandable implant 110 is in its second configuration than when the expandable implant is in its first configuration. The porosity of the porous mesh can be increased, for example, because one or more individual pores or openings are larger when in the second configuration than in the first configuration. For example, the porous mesh can be expanded in the second configuration, thereby increasing the space between filaments of the mesh (and thus the size of one or more openings of the mesh). In other words, an overall volume of pore openings can be increased. In another example, the porosity of the porous mesh can be increased because one or more openings that were closed off when the expandable implant 110 was collapsed into its first configuration are reopened when the expandable implant is moved to its second configuration. In other words, a number of open pores can be increased.

In some embodiments, the first portion 120 and the second portion 130 can have one of the same or different porosities. For example, the first portion 120 can have a porosity greater than a porosity of the second portion 130. In another example, the second portion 130 can have a porosity greater than the porosity of the first portion 120. In still another example, the first and second portions 120, 130 can have substantially equivalent porosities in the expanded configuration.

In some embodiments, at least one of the first portion 120 and the second portion 130 includes one, two, three, or more layers. For example, in some embodiments, the first portion 120 of the expandable implant 110 includes a first layer (not shown in FIG. 1 or 2) of porous mesh and a second layer (not shown in FIG. 1 or 2) of porous mesh. The first layer and the second layer can have the same or different porosities. In some embodiments, the first layer is offset from the second layer. As such, the porosity of the first portion is determined by the porosities of the first and second layers and the manner in which the first layer is offset from the second layer.

In some embodiments, at least a portion of the expandable implant 110, such as at least one of the first portion 120 or the second portion 130 can include a shape-memory material, such as, for example, nitinol, and can be preformed to assume a desired shape. Thus, in such an embodiment, the portion of the expandable implant 110 (e.g., the first portion 120 and/or the second portion 130) can be biased into an expanded second configuration and moved to a collapsed first configuration by restraining or compressing the portion of the expandable implant.

In some embodiments, at least a portion of the expandable implant 110, such as at least one of the first portion 120 or the second portion 130 can include an electropositive material, described in more detail below.

The expandable implant 110 when in the expanded configuration can have a variety of different shapes, sizes and configurations. For example, in some embodiments, when in the expanded configuration the expandable implant 110 can be substantially spherical. In some embodiments, the expandable implant 110 can be substantially helical. In some embodiments, the expandable implant 110 can be substantially circular, disc-shaped, or ring-shaped. In some embodiments, the expandable implant 110 can be a custom-made shape based on a shape of a target aneurysm within a patient; for example, a shape modeled after the shape of the target aneurysm as detected by an imaging device. For example, an image of the aneurysm shape can be acquired using an angiogram, and the expandable implant 110 can be modeled after the shape of the aneurysm shown in the angiogram. In some embodiments, the expandable implant 110 can include multiple portions having varying outer perimeters or outer diameters. For example, in some embodiments, when in the expanded configuration the expandable implant 110 can include a first portion having a first outer perimeter, a second portion having a second outer perimeter and a third portion having a third outer perimeter. In such an embodiment, the second outer perimeter can be smaller than each of the first outer perimeter and the third outer perimeter.

In one example use of the medical device 100, a catheter 104 can be inserted into a blood vessel and directed to a desired treatment site near a vascular defect, such as the aneurysm. The expandable implant 110 is inserted into an elongate lumen of the catheter 104 for delivery to the treatment site. A distal portion of the catheter 104 is positioned adjacent the aneurysm within the blood vessel. The expandable implant 110 is moved from a first position inside the catheter to a second position outside the catheter. When the expandable implant 110 is in its first position, each of the first portion 120 and the second portion 130 are in a first configuration. For example, in the first configuration, each of the first and second portions 120, 130 can be compressed or collapsed within the lumen of the catheter 104 and are substantially linear in configuration.

The expandable implant 110 can be oriented with respect to an opening in the vessel wall in fluid communication with the aneurysm such that the expandable implant can enter a sac of the aneurysm when the expandable implant 110 is moved to its second position. The expandable implant 110 can be moved from its first position to its second position with the assistance of the insertion portion 102 such that the expandable implant 110 is directed into and positioned within a sac of the aneurysm. When the expandable implant 110 is in its second position, the first and second portions each have a second configuration. For example, in the second configuration, each of the first and second portions 120, 130 can be expanded into a three-dimensional shape. The three-dimensional shape of the first portion 120 in the second configuration can be similar to or different from the three-dimensional shape of the second portion 130. In the second configuration, the first portion 120 of the expandable implant 110 substantially overlaps the second portion 130. In some embodiments, the second portion 130 is disposed in an interior region defined by the first portion when each of the first portion and the second portion are in their respective second configurations.

The first and second portions 120, 130 can be moved to their respective second configurations concurrently or sequentially. For example, in some embodiments, the second portion 130 is moved to its second configuration before the first portion 120 is moved to its second configuration. The expandable implant 110 can assume a biased expandable configuration such that the walls of the expandable implant 110 contact at least a portion of the wall of the aneurysm and/or such that a portion of the expandable implant is disposed over the neck of the aneurysm. The presence of the expandable implant 110 over the neck of the aneurysm can substantially reduce and/or prevent further blood flow from the parent vessel into the aneurysm sac because the expandable implant can act as a physical flow disruptor for blood flowing from the parent vessel and as a scaffold for endothelial cell attachment at the aneurysm neck to promote endothelialization of the neck/vessel wall. The insertion portion 102 can then be disconnected from a proximal end of the expandable implant 110 and removed through the catheter 104.

FIGS. 3, 4, 5A, 5B and 5C illustrate a medical device according to an embodiment. The medical device 200 can include all or some of the same features and functions as described above for medical device 100. The medical device 200 includes an insertion portion 202 and an expandable implant 210. The expandable implant 210 is removably coupled at its proximal end to a distal end of the insertion portion 202.

Figure 4:
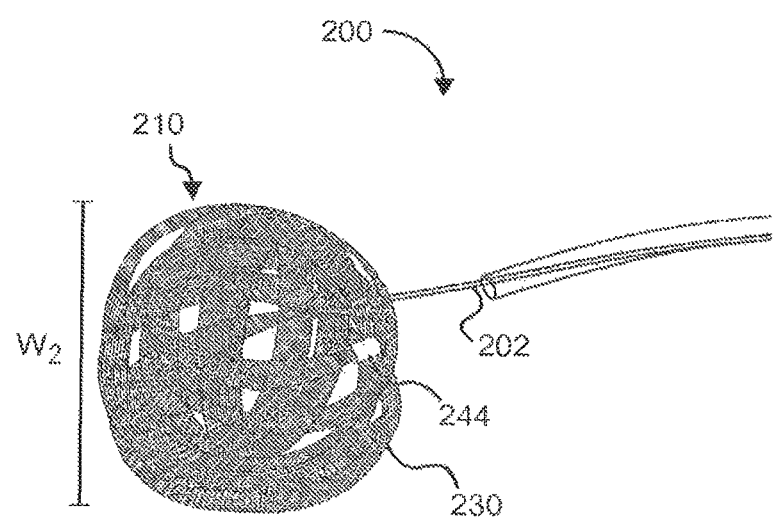
FIG. 4 is a side view of a medical device according to an embodiment in a second configuration.
Figure 5A:
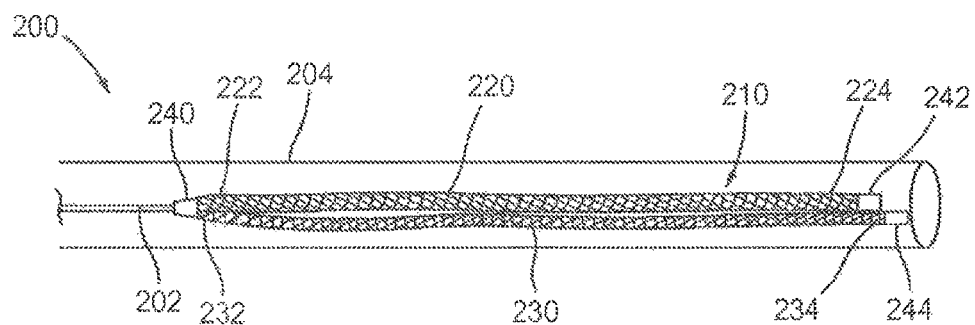
FIG. 5A is a view of the medical device of FIG. 3 in a first configuration during insertion into an aneurysm.
Figure 5B:
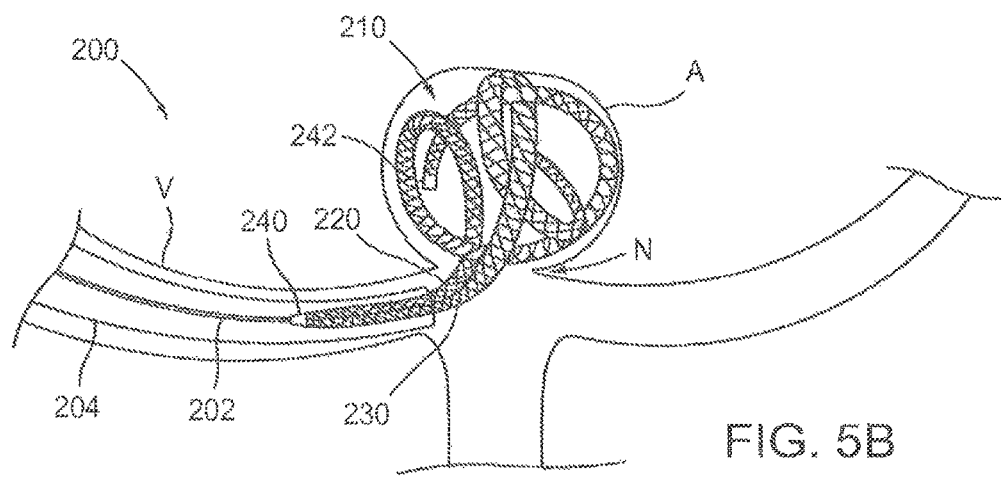
FIG. 5B is a view of the medical device of FIG. 3 in a second configuration during insertion into an aneurysm.

The expandable implant 210 includes a first portion 220 and a second portion 230. As shown in FIGS. 3 and 5A, the expandable implant 210 has a first, or collapsed, configuration in which the first and second portions 220, 230 are substantially linearly aligned. In this manner, the expandable implant 210 can be disposed within a lumen of a catheter 204 for delivery through a blood vessel V to a treatment site, such as to an aneurysm A. In its first configuration, the expandable implant 210 has a first width W1, as shown in FIG. 2. As shown in FIGS. 4 and 5B-5C, the expandable implant 210 is moveable to a second, or expanded or deployed, configuration. The insertion portion 202 is configured to move the expandable implant 210 from the first configuration to the second configuration. The insertion portion 202 can be disconnected from the expandable implant 210 when the expandable implant 210 is in its second configuration.

In its second configuration, the expandable implant 210 is configured to occupy at least a portion of the volume defined by a sac of the aneurysm A. As such, the expandable implant 210 has a second width W2 in the second, expanded, configuration greater than its first width Wi. For example, the expandable implant 210 can be substantially narrow and elongate in its first configuration and can assume a three-dimensional shape in its second configuration. In the embodiments illustrated in FIGS. 3-5C, the expandable implant 210 has a substantially spherical shape in its second configuration. The expandable implant 210 can be compliant such that its three-dimensional shape can accommodate any irregularities in the shape of the aneurysm. In the second configuration, the second portion 230 of the expandable implant 210 at least partially overlaps the first portion 220. At least a portion of the expandable implant 210 is configured to be positioned over a neck N of the aneurysm A when the expandable implant is in its second configuration within the sac of aneurysm A. The expandable implant 210 is configured to facilitate endothelial cell attachment at the neck N of the aneurysm A, as described in more detail herein.

In the embodiment illustrated in FIG. 3, the first portion (or member) 220 is a first ribbon-like strand and the second portion (or member) 230 is a second ribbon-like strand discrete from the first portion. In other embodiments, an expandable implant can include a first portion and a second portion from a single ribbon-like strand (e.g., integrally or monolithically constructed), instead of discrete portions. A first end 222 of the first portion 220 is coupled to a first end 232 of the second portion 230. Any suitable mechanism for coupling the first end 222 of the first portion 220 to the first end 232 of the second portion 230 can be used, such as an adhesive, a mechanical coupler, a weld, or the like, or any combination of the foregoing. For example, the first ends 222, 232 can be coupled by a band 240. The band 240 can also be configured to help couple the insertion portion 202 to the expandable implant 210. The band 240 can be or can include, for example, a radiopaque marker.

A second end 224 of the first portion 220 and a second end 234 of the second portion 230 each have a radiopaque marker 242, 244, respectively, coupled thereto. The radiopaque markers 242, 244 are configured to facilitate imaging of the expandable implant 210 during delivery to the treatment site and/or subsequent to implantation. The markers 242, 244 are configured to be wholly disposed within the sac of the aneurysm A when the expandable implant 210 is in its second configuration. As such, the markers 242, 244 will not puncture the a wall of the aneurysm A or the vessel V, and the markers 242, 244 will not interfere with endothelial cell attachment at the aneurysm neck. This is also beneficial because if the markers 242, 244 were positioned at or proximate to the neck of the aneurysm, blood from a parent blood vessel could have a tendency to clot around the marker.

When the expandable member 210 is moved between its first configuration and its second configuration, at least one of the first portion 220 and the second portion 230 is also moveable between a first configuration and a second configuration. The first portion or member 220 has a first, collapsed, configuration in which the first portion 220 is substantially elongate and has a first width. The first portion 220 has a second, expanded, configuration, in which the first portion 220 has a second width greater than the first width. For example, the first portion 220 can be moveable from a substantially linear, elongate collapsed configuration to a multi-dimensional (e.g., three-dimensional) shape in the expanded or deployed configuration. As shown in FIGS. 4 and 5C, the first portion 220 can have a three-dimensional shape in the expanded configuration that lends an overall spherical shape to the expandable implant 210. The first portion 220 can be biased to its second, expanded, configuration.

The first portion or member 220 is porous and, for example, can include or be constructed of a porous mesh. The porous mesh can be formed using filaments that are woven or braided together in a manner that openings or interstices are present between portions of the filaments at least when the expandable implant 210 is in its second configuration. For example, the porous mesh can include a plurality of braided wires. Suitable mesh material is described in more detail herein. The porous mesh can have a first porosity when the first portion 220 is in the first configuration and a second porosity when the first portion 220 is in the second configuration. For example, when the first portion 220 is moved from its first, collapsed, configuration to its second, expanded, configuration, the mesh can be expanded such that the size of the openings of the mesh is increased, thus increasing the porosity of the mesh. The porous mesh is configured to act as a scaffold that promotes clot formation and endothelium cell attachment when the mesh is disposed within the aneurysm A. Specifically, endothelial cells will migrate to the openings of the mesh.

The first portion 220 of the expandable implant 210 includes a first layer of porous mesh and a second layer of porous mesh. In this manner, the density of the first portion 220 is greater than the density of either the first or second layers individually. Such a dual-density structure can help to limit or prevent blood flow into the aneurysm A, for example when the first and second layers of the first portion 220 are disposed over the neck N of the aneurysm A. The first layer of porous mesh and the second layer of porous mesh can have the same porosities, or different porosities. The first layer of porous mesh can be offset from the second layer of porous mesh. In this manner, the overall porosity of the first portion 220 is greater than the porosity of either the first or second layers individually. The first and second layers of porous mesh can be coupled together in any suitable manner. For example, the first portion 220 can be formed using an elongate tubular mesh having an elongate lumen therethrough. In such an embodiment, the elongate mesh can be flattened from a tubular structure to a ribbon-like structure such that a first side, or layer, of the mesh is disposed on or proximate to a second side, or layer, of the mesh, thus forming a dual density, or dual-layered, mesh structure.

The second portion, or member, 230 of the expandable implant 210 can be configured the same as or similar to, and can be used in the same or similar manner, as the first portion 220. When the expandable member 210 is moved between its first configuration and its second configuration, the second portion 230 is also moveable between a first, collapsed, configuration in which the second portion is substantially elongate and has a third width, and a second, expanded, configuration, in which the second member has a fourth width greater than the third width. For example, the second portion 230 can be moveable from a substantially linear, elongate collapsed configuration to a multi-dimensional (e.g., three-dimensional) shape in the expanded configuration. As shown in FIGS. 4 and 5C, the second portion 230 can have a three-dimensional shape in the expanded configuration that lends an overall spherical shape to the expandable implant 210. The second portion 230 can be biased to its second, expanded, configuration.

The second portion 230 is porous and can include or be constructed of a porous mesh. The porous mesh can be configured the same as or similar to, and can be used in the same or similar manner, as the porous mesh described above with respect to the first portion 220 of the expandable implant 210. For example, the porous mesh can include a weave or braid of filaments that is porous at least when the expandable implant 210 is in its second configuration. Additionally, the porous mesh of the second portion 230 can have a first porosity when the second portion 230 is in the first configuration and a second porosity when the second portion 230 is in the second configuration. In some embodiments, the second portion 230 of the expandable implant 210 includes a first layer of porous mesh and a second layer of porous mesh, which can be of the same or different porosities. In this manner, the total density of the second portion 230 is greater than the density of either the first or second layers individually. The first layer of porous mesh can be offset from the second layer of porous mesh such that the overall porosity of the second portion 230 is greater than the porosity of either the first or second layers individually. Similarly as described above with respect to the first portion 220, the first and second layers of porous mesh of the second portion 230 can be formed from a monolithically constructed elongate tubular mesh that is flattened into a ribbon-like structure.

The first portion 220 and the second portion 230 of the expandable implant 210 can be the same or different sizes. For example, as shown in FIG. 5A, the first portion 220 can have a length in its first, collapsed, configuration, that is less than a length of the second portion 230 in its first, collapsed, configuration. In this manner, the markers 242, 244 will be sequentially introduced through the neck N of the aneurysm A, which permits the expandable implant 210 to be introduced through a narrower neck N. In another example, the first portion 220 and the second portion 230 can have the same or different widths. In some embodiments, for example, the first width of the first portion 220 in its first configuration is wider than the third width of the second portion 230 in its first configuration. The second width of the first portion 220 in its second configuration can also be wider than the fourth width of the second portion 230 in its second configuration. In another example, the fourth, expanded, width of the second portion 230 can be greater than the second, expanded, width of the first portion 220. In some embodiments, the porous mesh of the first portion 220 can have a multi-dimensional shape with a first width when the expandable implant 210 is in its second configuration, and the porous mesh of the second portion 230 can have a multi-dimensional shape with a second width less than the first width when the expandable implant is in its second configuration.

In some embodiments, for example, the first portion 220 (or the porous mesh of the first portion) can have a width of about 8 mm when the expandable implant is expanded in its second configuration, and the second portion 230 (or the porous mesh of the second portion) can have a width of about 9.5 mm when the expandable implant is expanded in its second configuration. As such, in an embodiment in which the first portion 220 has a smaller overall size in the expanded configuration than the second portion 230, the first portion 220 can be configured to be disposed within an open interior region formed by the second portion 230 in its second configuration.

In some embodiments, a variation of medical device 200 is contemplated. For example, in such an embodiment, the first portion of the expandable implant can include a first tubular mesh that defines a lumen therethrough, and the second portion of the expandable implant can include a second tubular mesh disposed within the lumen of the first tubular mesh. The first and second tubular mesh structures can be formed into a substantially ribbon-like strand. As such, the expandable implant has a four-layer density. The expandable implant can include additional ribbon-like strands in addition to the strand formed by the first and second portions. For example, the expandable implant can include one, two, three, four, five, six, seven, eight, or nine strands, with each of the strands having a desired number of layers (e.g., two, four, or more layers). As such, an expandable implant can be formed that has a desired amount of density. As noted above, a highly dense structure helps to prevent blood flow from the parent blood vessel into the aneurysm. Each layer or portion of the expandable implant can have the same or different density as the other layers or portions. Furthermore, each layer or portion of the expandable implant can have the same or different porosity as the other layers or portions.

Figure 6:
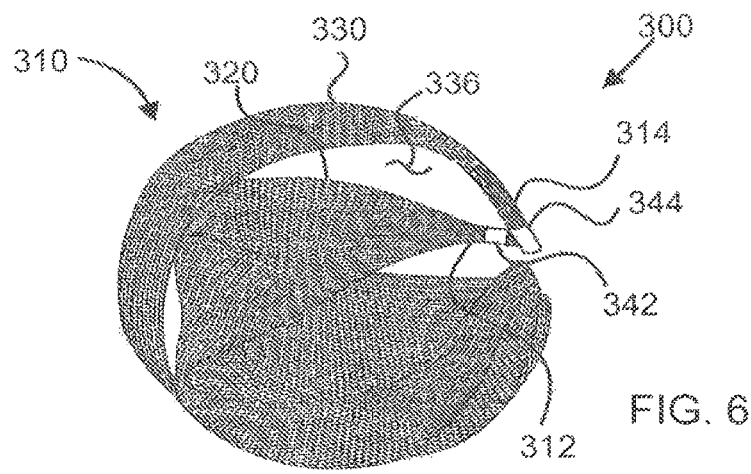
FIG. 6 is a view of a portion of a medical device in an expanded configuration, according to an embodiment.

FIG. 6 illustrates a portion of another embodiment of a medical device. The medical device 300 can include the same or similar features and functions as described above for previous embodiments. For example, the medical device 300 includes an expandable implant 310 and an insertion portion or member (not shown in FIG. 6). The expandable implant 310 is shown in an expanded configuration and can be moved between a compressed or collapsed configuration in which the expandable implant is substantially elongate and the expanded configuration in the same or similar manner as described above for expandable implant 210. In the expanded configuration, a first portion 320 of the expandable implant 310 is overlapped by a second portion 330 of the expandable implant. Additionally, at least a portion of the first portion 320 is disposed within an open interior region 336 defined by the second portion 320 when the expandable implant 310 is in its expanded configuration.

The expandable implant 310 includes a ribbon-like strand of porous mesh. At least a portion of the porous mesh is configured to be positioned over a neck of an aneurysm with the expandable implant 310 is in the expanded configuration. The porous mesh is configured to bend, curve, and/or twist at multiple turns into a substantially spherical shape when the expandable implant 310 is in the expanded configuration. The porous mesh can be a ribbon-like structure that is wider than the porous mesh of expandable implant 210. In this manner, the porous mesh of expandable implant 310 can be a shorter length than that of expandable implant 210 and still provide a similar amount of coverage within the aneurysm (and over the neck of the aneurysm) as expandable implant 210. The porous mesh can include one, two, or more layers depending on the desired density and porosity of the expandable implant 310. In some embodiments, a first radiopaque marker 342 is coupled to a first end 312 of the expandable implant 310 and a second radiopaque marker 344 is coupled to a second end 314 of the expandable implant. The expandable implant 310 is configured to be wholly disposed within the aneurysm such that the radiopaque markers 342, 344 are wholly disposed within the aneurysm sac and the porous mesh is disposed over the neck of the aneurysm. In some embodiments, the radiopaque markers are configured to be positioned at a side of the aneurysm (i.e., disposed away from the neck of the aneurysm).

Figure 7:
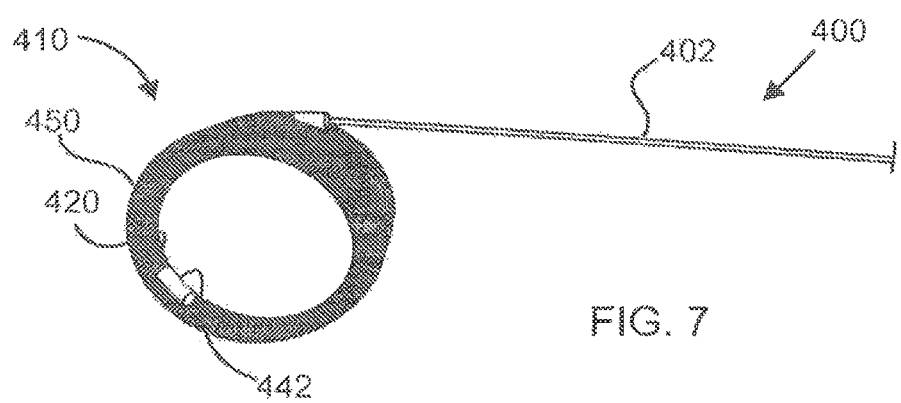
FIGS. 7-13 are views of a medical device in an expanded configuration, according to embodiments.

FIG. 7 illustrates another embodiment of a medical device. The medical device 400 can include the same or similar features and functions as described above for previous embodiments. For example, the medical device 400 includes an expandable implant 410 and an insertion portion or member 402. The expandable implant 410 is sized to occupy the sac of an aneurysm, and the insertion member 402 is configured to facilitate delivery of the expandable implant into the sac of the aneurysm. The expandable implant 410 is shown in an expanded configuration and can be moved between a compressed or collapsed configuration and the expanded configuration in the same or similar manner as described above for previous embodiments.

The expandable implant 410 includes at least one ribbon-like strand of porous mesh configured to be expanded within the aneurysm as a 360 degree spiral or ring-shaped structure. In the expanded configuration, a first portion 420 of the expandable implant 410 is overlapped by a second portion (not shown in FIG. 7) of the expandable implant, which is overlapped by a third portion 450 of the expandable implant. In this manner, at least a portion of the expandable implant 410 includes two, three, four, or more layers of implant material (e.g., porous mesh, as described above in previous embodiments), which can be positioned over the neck of the aneurysm from within the aneurysm to function as a dense flow disruptor. In some embodiments, a radiopaque marker 442 is coupled to the expandable implant 410.

Figure 8:
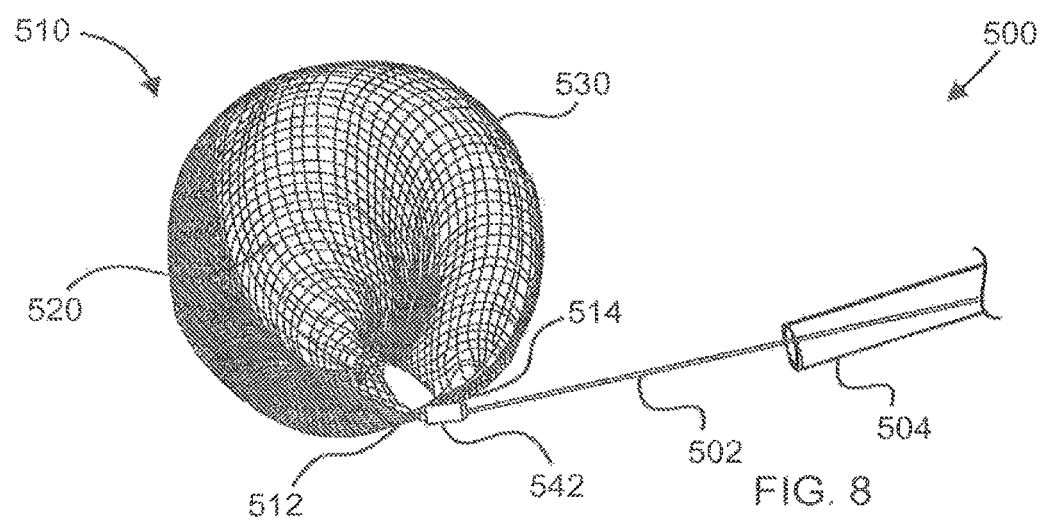

FIG. 8 illustrates another embodiment of a medical device. The medical device 500 can include the same or similar features and functions as described above for medical device 400. For example, the medical device 500 includes an expandable implant 510 and an insertion portion or member 502. The medical device 500 can be delivered to an aneurysm or other vascular defect using a microcatheter 504. The expandable implant 510 is sized to occupy at least a portion of the volume defined by the sac of the aneurysm, and the insertion member 502 is configured to facilitate delivery of the expandable implant into the sac of the aneurysm. The expandable implant 510 is shown in an expanded configuration and can be moved between a compressed or collapsed configuration and the expanded configuration in the same or similar manner as described above for previous embodiments.

The expandable implant 510 includes a porous mesh configured to be expanded within the aneurysm as a substantially circular or disc-shaped structure, as shown in FIG. 8. In the expanded configuration, a first end portion 512 of the expandable implant 510 is engaged with and/or overlapped with a second end portion 514 of the expandable implant. The expandable implant 510 includes a first portion 520 having a first density of porous mesh and a second portion 530 having a second, higher, density of porous mesh. More specifically, a weave or braid of the porous mesh has a higher density in the second portion 530 than in the first portion 520 of the expandable implant. The expandable implant 510 is configured to be disposed within the aneurysm (or other vascular defect) such that at least a portion of the second portion 530 is disposed over the neck of the aneurysm, because the higher density promotes endothelial cell attachment to the expandable implant. The expandable implant 510 includes at least one radiopaque marker 542, which can be disposed on one of the first end portion 512 (as shown in FIG. 8) and/or the second end portion 514. When the expandable implant 510 is disposed within the aneurysm in its expanded configuration such that the higher density second portion 530 is disposed over the neck of the aneurysm, the at least one radiopaque marker 542 is disposed within the sac of the aneurysm away from the neck of the aneurysm.

Figure 9:
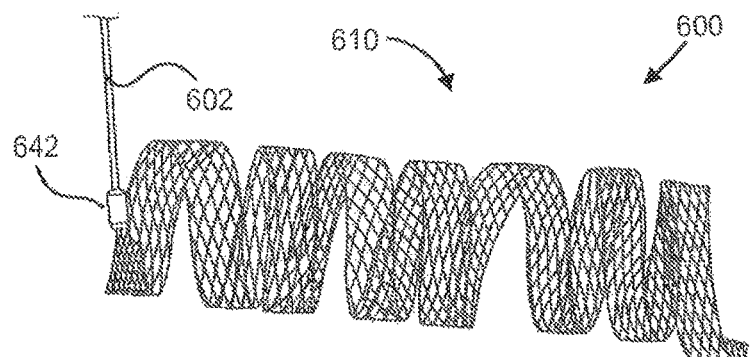

FIG. 9 illustrates another embodiment of a medical device. The medical device 600 can include the same or similar features and functions as described above for previous embodiments. For example, the medical device 600 includes an expandable implant 610 and an insertion portion or member 602. The expandable implant 610 is sized to occupy at least a portion of a volume defined by the sac of the aneurysm, and the insertion member 602 is configured to facilitate delivery of the expandable implant into the sac of the aneurysm. The expandable implant 610 is shown in an expanded configuration and can be moved between a compressed or collapsed configuration and the expanded configuration in the same or similar manner as described above for previous embodiments.

The expandable implant 610 includes a ribbon-like strand of porous mesh having at least two layers of mesh. The expandable implant 610 is configured to be expanded within the aneurysm as a substantially helical or coil shaped structure, as shown in FIG. 9. The expandable implant 610 can be disposed within the aneurysm (or other vascular defect) such that at least a portion of the implant is disposed over the neck of the aneurysm to facilitate endothelial cell attachment at the neck. The expandable implant 610 includes at least one radiopaque marker 642, which can be disposed on an end of the expandable implant 610, as shown in FIG. 9. The insertion member 602 can be removably coupled to the expandable implant at the radiopaque marker.

Figure 10:
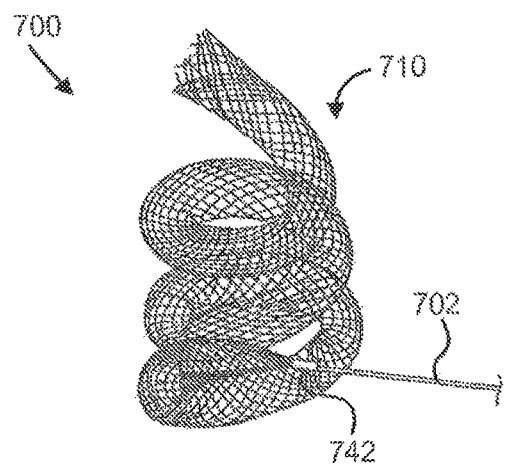

FIG. 10 illustrates another embodiment of a medical device. A medical device 700 includes all the same or similar features and functions as described above for medical device 600. For example, the medical device 700 includes an expandable implant 710, an insertion portion or member 702, and a radiopaque marker 742 coupled to an end of the expandable implant. The expandable implant 710 includes a porous mesh formed of a tubular or rounded braid structure. The rounded braid structure can lend more softness to the expandable implant 710 than, for example, the flattened ribbon-like structure previously described.

Figure 11:
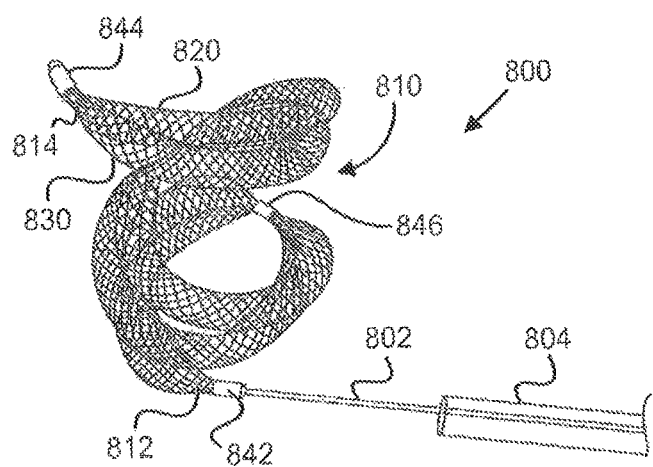

FIG. 11 illustrates another embodiment of a medical device. The medical device 800 can include the same or similar features and functions as described above for previous embodiments. For example, the medical device 800 includes an expandable implant 810 and an insertion portion or member 802. The medical device 800 can be delivered to an aneurysm or other vascular defect using a microcatheter 804. The expandable implant 810 is sized to occupy at least a portion of the volume of the sac of the aneurysm, and the insertion member 802 is configured to facilitate delivery of the expandable implant from the microcatheter 804 into the sac of the aneurysm. The expandable implant 810 is shown in an expanded configuration and can be moved between a compressed or collapsed configuration and the expanded configuration in the same or similar manner as described above for previous embodiments.

The expandable implant 810 includes a first member 820 and a second member 830. The first and second members 820, 830 are coupled at a first end 812 of the expandable implant 810 and a second end 814 of the expandable implant. The first and second members 820, 830 are also coupled together for at least one middle portion of the expandable implant 810 between the first end 812 and the second end 814. The first and second members 820, 830 can be coupled, for example, using radiopaque markers 842, 844, 846. Each site of coupling is configured to be a folding point of the expandable implant 810 when the expandable implant is delivered into the aneurysm and is expanded within the aneurysm to comply with the shape of the aneurysm. As such, the expandable implant 810 can be more densely packed into the aneurysm, for example, as compared to an implant that cannot bend or fold in response to the shape of the aneurysm. At least one of the first member 820 and the second member 830 of the expandable implant 810 includes a porous mesh formed of a tubular or rounded braid structure.

Figure 12:
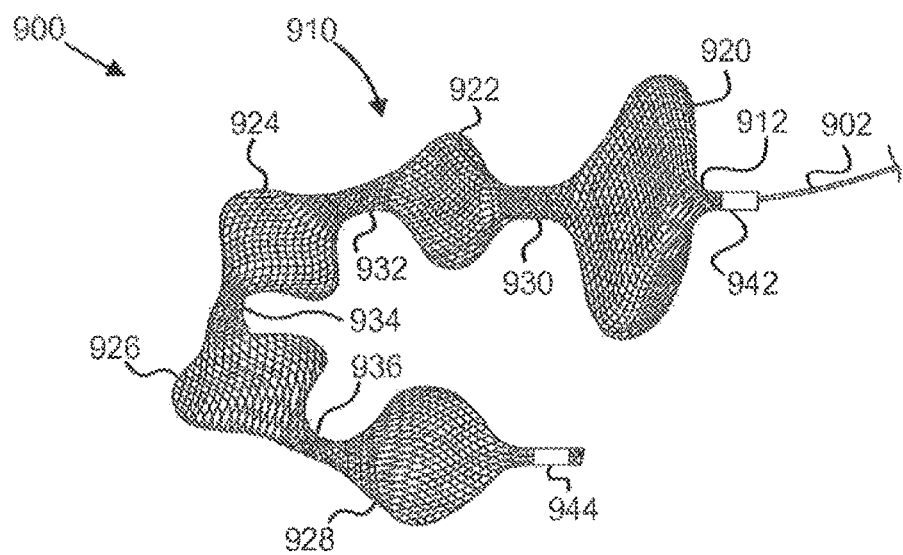

FIG. 12 illustrates another embodiment of a medical device. The medical device 900 can include the same or similar features and functions as described above for previous embodiments. For example, the medical device 900 includes an expandable implant 910 and an insertion portion or member 902. The expandable implant 910 is sized to occupy the sac of the aneurysm, and the insertion member 902 is configured to facilitate delivery of the expandable implant from a microcatheter (not shown in FIG. 12) into the sac of the aneurysm. The expandable implant 910 is shown in an expanded configuration and can be moved between a compressed or collapsed configuration and the expanded configuration in the same or similar manner as described above for previous embodiments.

The expandable implant 910 includes a series of expandable portions 920, 922, 924, 926, 928 separated by a series of constricted portions 930, 932, 934, 936. The expandable portions 920, 922, 924, 926, 928 can be configured to expand to any suitable multi-dimensional shape, including, for example, that resembling a sphere, a disc, a parabola, or the like. Additionally, each expandable portion 920, 922, 924, 926, 928 can have an expanded shape distinct from an expanded shape of another expandable portion.

When the expandable implant 910 is in its expanded configuration, as shown in FIG. 12, the expandable portions 920, 922, 924, 926, 928 are more porous and less dense then the constricted portions 930, 932, 934, 936. The density and/or porosity of each expandable portion 920, 922, 924, 926, 928 can be varied from the other expandable portions 920, 922, 924, 926, 928, and the density and/or porosity of each expandable portion 920, 922, 924, 926, 928 can be varied along a length and/or width of the respective expandable portion. For example, a first expandable portion 920 can be more dense and/or less porous proximate to a first constriction portion 930 and less dense and/or more porous at a middle, wider portion of the first expandable portion 920. Additionally, the expandable portions 920, 922, 924, 926, 928 are each configured to have a width greater than when the expandable implant 910 is in its collapsed configuration, and the constricted portions 930, 932, 934, 936 are each configured to have a width narrower than a width of the expandable portions 920, 922, 924, 926, 928. As such, the expandable implant 910 is configured to bend, curve, and/or fold at the constricted portions 930, 932, 934, 936 to help comply with the shape of the aneurysm.

When the expandable implant 910 is in its expanded configuration, the first expandable portion 920 is configured to have a width greater than the width of the other expandable portions 922, 924, 926, 928. The first expandable portion 920 can be, as illustrated in FIG. 12, the most proximal of the expandable portions 920, 922, 924, 926, 928. The first expandable portion 920 is configured to be positioned over a neck of the aneurysm when the expandable implant 910 is disposed within the aneurysm in its expanded configuration. In this manner, the first expandable portion 920 is configured to act as a flow disruptor at the neck of the aneurysm to help limit the flow of blood into the aneurysm from the parent blood vessel. The remaining, more distal, expandable portions 922, 924, 926, 928 are configured to be packed into the aneurysm to embolize the aneurysm.

The expandable implant 910 includes a first radiopaque marker 942 coupled to a first end 912 of the implant and a second radiopaque marker coupled to a second end 914 of the implant. The radiopaque markers 942, 944 are configured to be wholly disposed within the sac of the aneurysm when the expandable implant 910 is disposed in the aneurysm in its expanded configuration.

Figure 13:
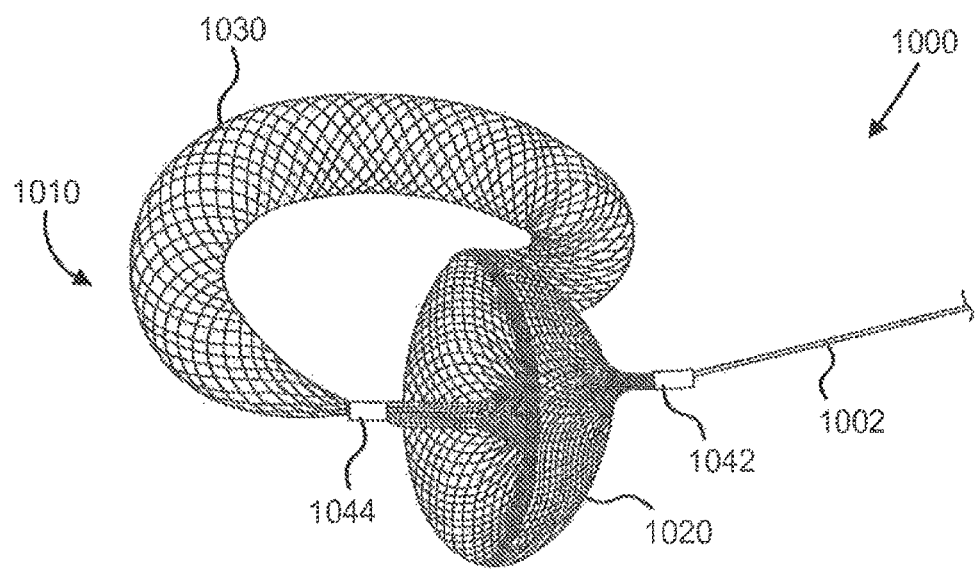

FIG. 13 illustrates another embodiment of a medical device. The medical device 1000 can include the same or similar features and functions as described above for previous embodiments. For example, the medical device 1000 includes an expandable implant 1010 and an insertion portion or member 1002. The expandable implant 1010 is sized to occupy the sac of the aneurysm, and the insertion member 1002 is configured to facilitate delivery of the expandable implant into the sac of the aneurysm. The expandable implant 1010 is shown in an expanded configuration and can be moved between a compressed or collapsed configuration and the expanded configuration in the same or similar manner as described above for previous embodiments.

The expandable implant 1010 includes a first porous member 1020 and a second porous member 1030. The first porous member 1020 includes a porous mesh configured to have a multi-dimensional shape when the expandable implant 1010 is in its expanded configuration. As such, the first porous member 1020 has a second width in the expanded configuration that is greater than a first width of the first porous member in the collapsed configuration. The first porous member 1020 can be configured to expand to any suitable multi-dimensional shape, including, for example, that resembling a parabola, as shown in FIG. 13, a sphere, a disc, or the like. The first porous member 1020 is configured to be positioned over a neck of the aneurysm when the expandable member 1010 is disposed within the sac of the aneurysm to disrupt and/or stop the flow of blood into the aneurysm from the parent blood vessel. Additionally, the porous mesh of the first porous member 1020 is configured to promote endothelial cell attachment at the neck of the aneurysm, which can help to heal over the neck of the aneurysm.

The second porous member 1030 includes a porous mesh configured to have a multi-dimensional shape when the expandable implant 1010 is in its expanded configuration. As such, the second porous member 1030 has a fourth width in the expanded configuration greater than a third width of the second porous member in the collapsed configuration. The second porous member 1030 can be configured to expand to any suitable multi-dimensional shape, including, for example, that resembling a tube, as shown in FIG. 13, a sphere, a disc, a parabola, or the like. In the embodiment illustrated in FIG. 13, the second width of the first porous member 1020 is greater than the fourth width of the second porous member 1030. The second porous member 1030 is configured to be disposed within the sac of the aneurysm such that the first porous member 1020 is disposed between the second porous member 1030 and the neck of the aneurysm. The second porous member 1030 is configured to be packed into the aneurysm to embolize the aneurysm.

A radiopaque marker 1044 is disposed between the first porous member 1020 and the second porous member 1030, and can be used to couple the first and second porous members. The expandable implant 1010 is configured to bend, curve, and/or fold at the radiopaque marker 1044, which can help the expandable implant 1010 comply with the shape of the sac of the aneurysm. Another radiopaque marker 1042 can be disposed on a proximate end of the expandable implant 1010, and can be used to couple the insertion portion 1002 to the expandable implant. The radiopaque markers 1042, 1044 are configured to be wholly disposed within the sac of the aneurysm when the expandable implant 1010 is disposed in the aneurysm in its expanded configuration.

Figure 14:
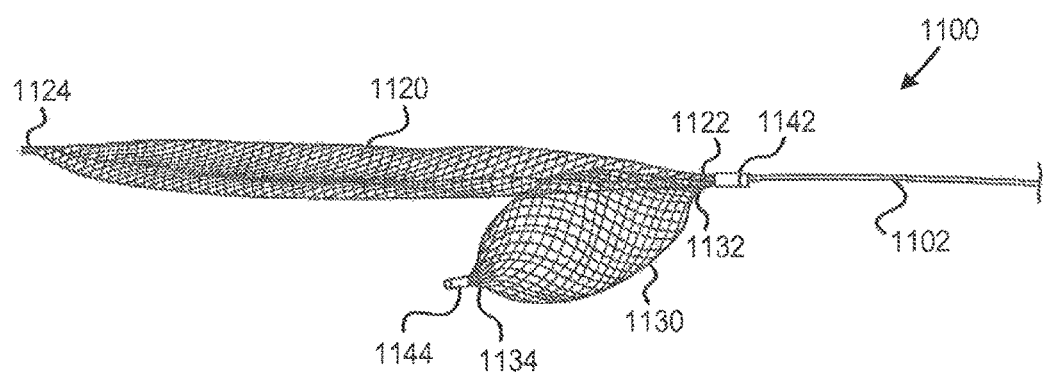
FIG. 14 is a view of a medical device in a partially collapsed configuration, according to an embodiment.
Figure 15:
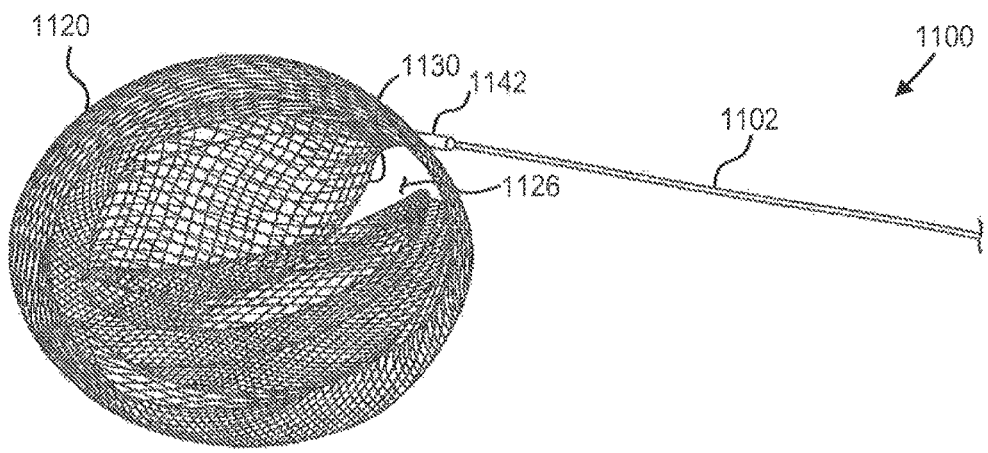
FIG. 15 is a view of the medical device of FIG. 14 in an expanded configuration, according to an embodiment.

FIGS. 14-15 illustrate another embodiment of a medical device. The medical device 1100 can include the same or similar features and functions as described above for previous embodiments. For example, the medical device 1100 includes a first porous member 1120, a second porous member 1130, and an insertion portion or member 1102 removably couplable to the first and second porous members 1120, 1130.

The first porous member 1120 has a first end 1122 and a second end 1124. As shown in FIG. 14, the first porous member 1120 has a collapsed configuration for insertion through a blood vessel. In its collapsed configuration, the first porous member 1120 is substantially elongate with a first length. As shown in FIG. 15, the first porous member 1120 has an expanded configuration for occupying a sac of an aneurysm. When the first porous member 1120 is in its expanded configuration, it has a three-dimensional shape and defines an open interior region 1126. The first porous member 1120 can have any suitable three-dimensional shape. For example, the first porous member 1120 can be configured to curved into a substantially spherical shape, as shown in FIG. 15. Additionally, in its expanded configuration, the first porous member 1120 includes a first segment configured to overlap with a second segment, which can be similar in many respects as described above with respect to expandable implants 210 and 310, for example For example, the first porous member 1120 can include a mesh having a first segment configured to overlap with a second segment of the porous mesh to form a higher density portion of the first porous member 1120.

The second porous member 1130 has a first end 1132 and a second end 1134. The second porous member 1130 has a collapsed, first, configuration (not shown in FIG. 14 or 15) for insertion through a blood vessel. In its collapsed configuration, the second porous member 1130 is substantially elongate with a second length less than the first length of the first porous member, and is configured to occupy a first volume. As shown in FIGS. 14 and 15, the second porous member 1130 has an expanded, second, configuration for occupying at least a portion of the volume of the sac of the aneurysm. When the second porous member 1130 is in its expanded configuration, it has a three-dimensional shape and is configured to occupy a second volume greater than the first volume. The second porous member 1130 can have any suitable three-dimensional shape. For example, the second porous member 1130 can be configured to expand into a substantially ball (e.g., spherical, round, oblong, or the like) shape, as shown in FIGS. 14 and 15. In the expanded configuration, the second porous member 1130 can have a porosity the same as, or different than, a porosity of the first porous member 1120. The second porous member 1130 is configured to be disposed in the interior region 1126 of the first porous member 1120 when each of the first porous member and the second porous member are in the deployed or expanded configurations.

In the embodiment illustrated in FIGS. 14 and 15, the second porous member 1130 is coupled to the first porous member 1120. Specifically, the first end 1122 of the first porous member 1120 is coupled to the first end 1132 of the second porous member 1130. At least one of the first porous member 1120 and the second porous member 1130 includes a radiopaque marker. As shown in FIG. 14, a first radiopaque marker 1142 can be disposed on the first ends 1122, 1132 of the first and second porous members 1120, 1130 to couple the first and second porous members together. A second radiopaque marker 1144 can be disposed on the second end 1134 of the second porous member 1130. When the first and second porous members 1120, 1130 are in their respective expanded configurations, the second radiopaque marker 1144 is disposed within the interior region defined by the first porous member 1120.

In use, the first and second porous members 1120, 1130, and the first and second radiopaque markers 1142, 1144, are wholly disposed within the aneurysm. The second porous member 1130 can be inserted into the aneurysm first and assume its expanded configuration therein. The first porous member 1120 can then be inserted into the aneurysm such that the first porous member curves, coils, or otherwise wraps around the second porous member 1130 as the first porous member moves to its expanded configuration. The first porous member 1120 is configured to be disposed within the aneurysm such that a portion of the first porous member is disposed over the neck of the aneurysm. For example, the higher density portion of the first porous member 1120 at which the first segment overlaps the second segment can be positioned over the neck of the aneurysm to promote endothelial cell attachment at the aneurysm neck. The second porous member 1130 can help to embolize the aneurysm by providing additional porous mesh within the sac of the aneurysm for cell attachment and/or clot formation. As such, the second porous member occupies a portion of the volume of the sac of the aneurysm such that blood flow through the aneurysm is further inhibited.

Although the medical device 1100 includes discrete first and second porous members 1120, 1130, respectively, in other embodiments, the first and second porous members can be differently constructed. For example, referring to FIG. 16, an embodiment of a medical device 1200 is illustrated. The medical device 1200 can include the same or similar features and functions as described above for medical device 1100, or other previous embodiments. For example, the medical device 1200 includes a first porous member 1220, a second porous member 1230, and an insertion portion or member (not shown in FIG. 16) removably couplable to the first and second porous members. Each of the first porous member 1220 and the second porous member 1230 can be similar in form and function as the first porous member 1120 and the second porous member 1130, respectively, described above.

Figure 16:
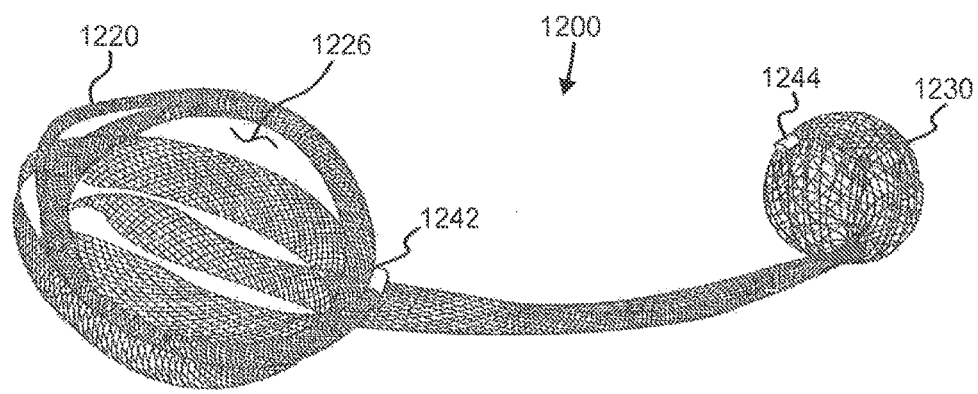
FIG. 16 is a view of a portion of a medical device in an expanded configuration according to an embodiment, with a first portion spaced apart from a second portion.

In the embodiment illustrated in FIG. 16, however, the second porous member 1230 is monolithically constructed with the first porous member 1220. It should be noted that in FIG. 16, the first and second porous members 1220, 1230, are shown in an expanded configuration but the second porous member 1230 is shown spaced apart from the first porous member 1220 for illustration purposes only. In use, in their respective deployed or expanded configurations, the second porous member 1230 is disposed within an interior region 1226 defined by the first porous member 1220 in a similar manner as that illustrated in FIG. 15 with respect to medical device 1100. Additionally, the medical device 1200 includes two radiopaque markers 1242, 1244. A first radiopaque marker 1242 is disposed at an end of a porous mesh of the first porous member 1220, and the second radiopaque marker 1244 is disposed at an opposing end of porous mesh of the second porous member 1230.

Figure 17A:
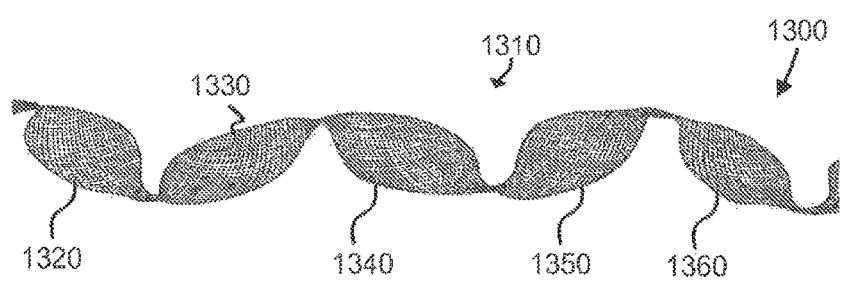
FIG. 17A is a view of a portion of a medical device in a collapsed configuration according to an embodiment.
Figure 17B:
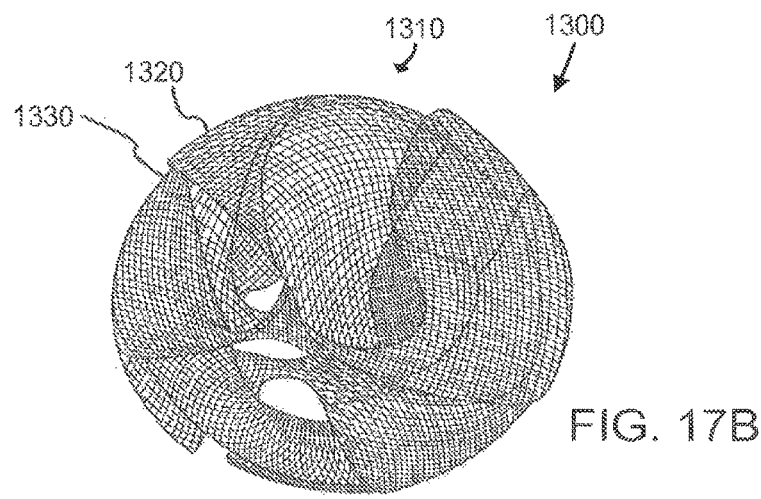
FIG. 17B is a view of a portion of a medical device in an expanded configuration according to an embodiment.

In some embodiments, a medical device includes an expandable implant that has a substantially continuous outer surface when in an expanded configuration. Referring to FIGS. 17A and 17B, a portion of a medical device 1300 according to an embodiment is illustrated in a collapsed configuration and an expanded configuration, respectively. The medical device 1300 can include the same or similar features and functions as described herein for other embodiments. For example, the medical device 1300 can include an expandable implant 1310 configured to move from the collapsed configuration (e.g., for delivery through a blood vessel) to the expanded configuration (e.g., for deployment within an aneurysm). The expandable implant 1310 includes at least a first portion 1320 and a second portion 1330, and can include additional portions 1340, 1350, 1360. When the expandable implant 1310 is in its expanded configuration, the expandable implant 1310 has a three-dimensional shape (e.g., a substantially spherical shape) with a substantially continuous outer surface such that edges of at least two of the portions 1320, 1330, 1340, 1350, 1360 overlap. For example, edges of the first portion 1320 and the second portion 1330 can overlap, as shown in FIG. 17B. In other words, the expandable implant 1310 moves into the expanded configuration such that few or no openings or spaces remain between edges of the portions 1320, 1330, 1340, 1350, 1360 of the expandable implant 1310.

Figure 18:
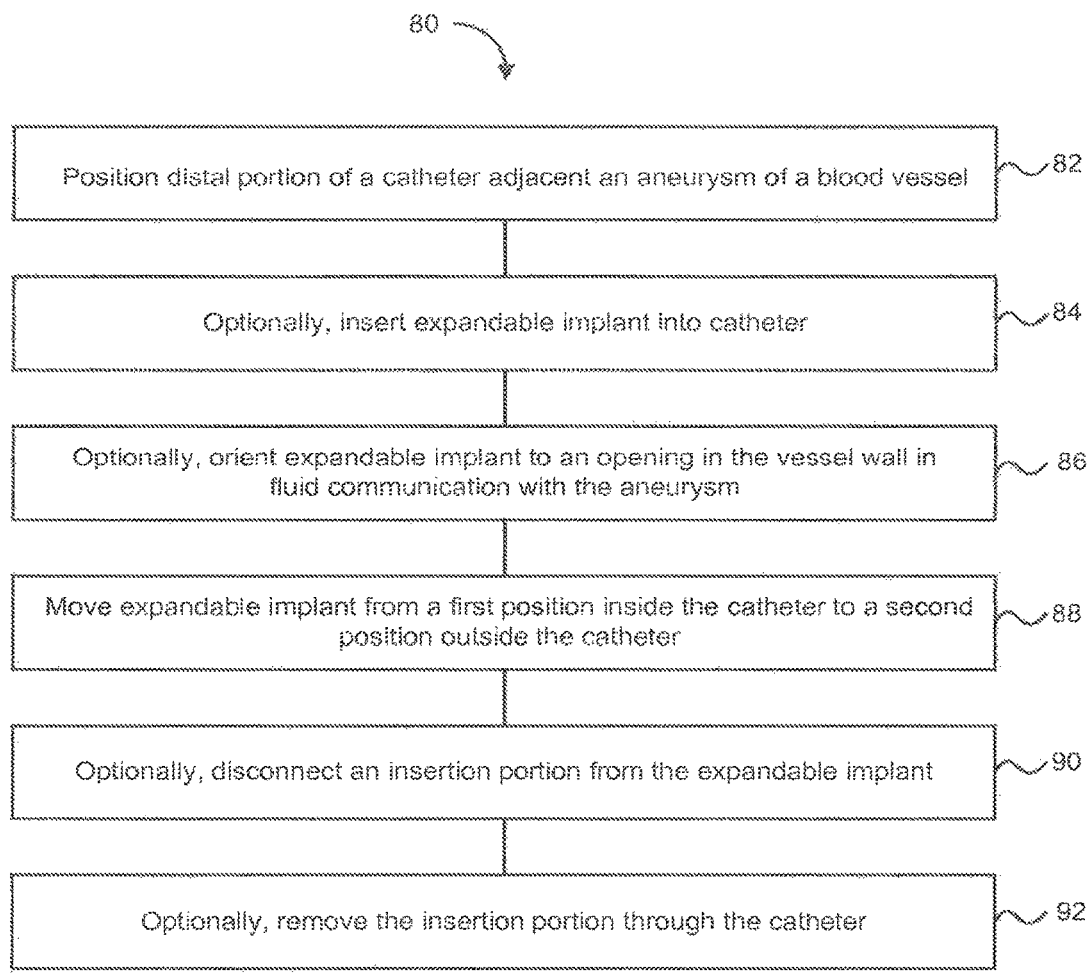
FIG. 18 is a flowchart of a method according to an embodiment.

FIG. 18 is a flowchart illustrating a method 80 of using a medical device to disrupt blood flow into an aneurysm and to promote healing of the aneurysm, as described herein, according to an embodiment. The method 80 includes at 82, positioning a catheter adjacent to an aneurysm of a blood vessel. For example, a distal portion of the catheter can be positioned adjacent an opening from the blood vessel into the aneurysm. The catheter defines an elongate lumen, which can be configured to receive at least a portion of the medical device for delivery to the aneurysm.

At 84, optionally, an expandable implant of the medical device is inserted into the catheter. The expandable implant includes a first portion and a second portion, each of which has a first (e.g., insertion or collapsed) configuration and a second (e.g., deployed or expanded) configuration. In the second configuration, the first portion substantially overlaps the second portion. Each of the first portion and the second portion also include a porous mesh. The porous mesh has a first porosity when in the first configuration and a second porosity when in the second configuration. The second porosity can be, for example, greater than the first porosity. The expandable implant can be biased in its second configuration before being inserted into the catheter. The expandable implant is in its first configuration when the expandable implant is disposed in the lumen of the catheter. The expandable implant can be inserted into the catheter after the catheter is positioned within the blood vessel, before the catheter is introduced into the blood vessel, or any time therebetween.

At 86, the expandable implant is optionally oriented to the opening in the vessel wall in fluid communication with the aneurysm. In this manner, the expandable implant is oriented to enter a sac of the aneurysm when the expandable implant is moved out of the catheter, as described in more detail herein.

At 88, the expandable implant is moved from a first position inside the catheter to a second position outside the catheter. For example, the expandable implant can be moved from a first position inside the lumen of the catheter to a second position in at least one of the blood vessel or the aneurysm outside of the catheter. As noted above, the expandable implant is in its first configuration when in its first position inside the catheter. The expandable implant is moved to its second configuration when in its second position outside of the constraint of the catheter. The second portion of the expandable implant can be moved to its second configuration before the first portion is moved to its second configuration. In their respective second configurations, the second portion can be disposed in an interior region defined by the first portion. For example, the second portion can be moved to its second configuration in which it has a multi-dimensional expanded shape, and then the first portion can be moved to its second configuration in which it curves into a multi-dimensional expanded shape around the second portion.

The medical device can include an insertion portion configured to move the expandable implant from its first position to its second position. The insertion portion can be, for example, a wire coupled to one of the first portion or the second portion of the expandable implant. At 90, the insertion portion is optionally disconnected from the expandable implant. For example, the insertion portion can be disconnected from a proximal end of the expandable implant, such as after the expandable implant has been inserted into the aneurysm. At 92, the insertion portion is optionally removed from the blood vessel through the catheter.

After the expandable implant is disposed within the aneurysm, or other target vascular defect, the portion of a patient's body including the aneurysm can be imaged (e.g., using X-ray or other suitable imaging techniques) to determine whether the expandable implant is properly positioned within the aneurysm. For example, the expandable implant can include one or more radiopaque markers that are visible using X-ray. In another example, the patient can be injected intravenously with a radiopaque dye at a desired time following implantation of the expandable implant to determine the success of endothelial cell attachment and/or healing over of the neck of the aneurysm following the procedure. If radiopaque dye is visible within the parent blood vessel adjacent the aneurysm, but not within the aneurysm itself, the expandable implant has operated to successfully prevent further blood flow into the aneurysm. If radiopaque dye is visible within the aneurysm, blood flow from the parent blood vessel has not been completely prevented and additional treatment options may be considered by the health care practitioner.

The various devices described herein can be made of any material suitable for the defined purpose, including, for example, drawn filed tube DFT®. DFT is available as wire, cable or ribbon. DFT is a metal-to-metal composite developed to combine the desired physical and mechanical attributes of two or more materials into a single wire or ribbon system, which can be used for the expandable implant.

Filaments or wires for the braid or mesh (e.g., the expandable implants) can include, for example, filaments of materials such as MP35N, stainless steel, nitinol, cobalt chromium, titanium, platinum, tantalum, tungsten, or alloys thereof, or polyester, polyethylene (PET), Dacron, PEEK, vectron, and suture materials. Each strand may have a diameter between 0.0005"-0.010", e.g., about 0.002". In some embodiments, an outer material of the mesh or braid can be formed with nitinol that is super elastic at body temperature, and an inner material can be radiopaque, or alternatively platinum wires may be included in the braid to provide additional radiopacity.

Suitable materials can be chosen based on their electropositivity. For example, an expandable implant can include titanium, tungsten, or another material listed below in Table 1, or any combination thereof. In use, the electropositive material of the expanded expandable implant creates an electrically favorable region within the vascular defect and through the blood, and the region in the defect containing blood, fluid or tissue is then predisposed for endothelialization to occur.

TABLE 1

| PERIODIC TABLE ELEMENT | ABBREVIATION | FULL NAME | COMPOSITE CHARGE VALUE |
|---|---|---|---|
| 22 | Ti | titanium | 1.36 |
| 23 | V | vanadium | 1.53 |
| 40 | Zr | zirconium | 1.22 |
| 41 | Nb | niobium or columbium | 1.33 |
| 42 | Mo | molybdenum | 1.47 |
| 72 | Hf | hafnium | 1.16 |
| 73 | Ta | tantalum | 1.30 |
| 74 | W | tungsten | 1.47 |

In some embodiments, the expandable implants described herein can be formed with tubular braid, or sheets of woven filaments (forming a mesh, weave or fabric). The filaments can be wire or polymer or other suitable material. The expandable implants can be braided wire (e.g. NiTi wire), and can include a mixture of wire types and wire sizes (e.g. NiTi and Platinum wire, and e.g. 0.001" wire braided with 0.00125" wire). The expandable implants can also be made with polymer fibers, or polymer fibers and metal wire mixed together.

The mesh of the expandable implants can be made by a variety of different forms, including, but not limited to, braiding, weaving, welding, or laser cutting. The mesh can have an operating length, for example, in a range of about 0.5 cm to about 70 cm. In some embodiments, the mesh can have a length of 30 cm. In some embodiments, the mesh can have a diameter in a range of about 0.5-60 mm. In some embodiments, the mesh can have a diameter of up to about 10 mm when expanded (e.g., about 9.5 mm for an outer porous member or portion, about 8 mm for an inner porous member or portion). The mesh can have a single density or can have two or more densities. For example, in some embodiments, the number of variable densities can be in a range of about 2 to about 10. For example, a first density can be about 100 PPI and a second density can be about 40 PPI. (PPI=pies per inch). The braid pattern can be any pattern suitable, for example, a one-over-one configuration, or two-over-one configuration, etc. Strand count for the mesh can be in a range of about 4 strands to about 288 strands. In some embodiments, the strand count is about 48 strands. Common multiples of 4, 8, 16, 24, 32, 64, 72, 96, 128, 144, 192 and 288 strands for braid are available using commercial braiders.

A single expandable implant can include wires of the same size or a combination of 2 different wire sizes. For example, the expandable implant can have 24 wires of 0.001" and 24 wires of 0.0005". The thicker wires can impart additional strength to the expandable implant and the thinner wire can provide density. In addition, any combination of wire count, wire diameter, braid angle or pick per inch can be used to make the mesh of the expandable implant.

CONCLUSION

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. For example, the expandable implant can be inserted into the catheter concurrently with positioning of the expandable catheter adjacent the aneurysm.

The embodiments have been particularly shown and described, but it will be understood that various changes in form and details may be made. For example, although various embodiments have been described as having particular features and/or combinations of components, other embodiments are possible having any combination or sub-combination of any features and/or components from any of the embodiments described herein. The specific configurations of the various components can also be varied.

For example, although the embodiments (e.g., medical device 1010) illustrated and described herein include one or two porous members or portions (e.g., porous members 1020, 1030), in other embodiments, any suitable number of porous members or portions can be included. For example, in some embodiments, the medical device 1010 can also include a third porous member (not shown) having a first end and a second end and coupled to at least one of the first porous member 1020 and the second porous member 1030. Like the first and second porous members 1020, 1030, the third porous member can have a collapsed configuration for insertion through the blood vessel and an expanded configuration for occupying the sac of the aneurysm. The third porous member can be substantially elongate and have a width in its expanded configuration that is greater than its width in its collapsed configuration.

In another example, a radiopaque marker of a medical device illustrated and described can be differently positioned on an expandable implant of the medical device. Moreover, the size and specific shape of the various components can be different than the embodiments shown, while still providing the functions as described herein.

The invention claimed is:

1. A device for treating an aneurysm of a human patient, the device comprising:
   an implant configured to be positioned within the aneurysm, the implant having a collapsed configuration and an expanded configuration, wherein, in the collapsed configuration, the implant is configured to be contained within a delivery device, wherein the implant includes a proximal portion configured to be removably coupled to a delivery device;
   a first braid having a proximal region fixed at the proximal portion and a distal region opposite the proximal region along the length of the first braid;
   a second braid having a proximal region fixed at the proximal portion and a distal region opposite the proximal region along the length of the second braid;
   wherein at least one of the first braid and the second braid comprises a flattened tubular braid configured to form a three-dimensional structure when the implant is in the expanded configuration; and
   wherein, when the implant is in the collapsed configuration, the first braid and the second braid are coextensive along at least a portion of each other.

2. The device of claim 1 wherein the first braid and the second braid are separate, discrete braids coupled at the proximal portion of the implant.

3. The device of claim 1 wherein the first braid or the second braid comprises a tubular braid configured to form a three-dimensional structure when the implant is in the expanded configuration.

4. The device of claim 1 wherein
   the first braid comprises the tubular braid;
   the second braid comprises a flattened tubular braid;
   the second braid is configured to expand within the aneurysm and form a spherical structure, wherein the spherical structure defines an interior volume; and
   the first braid is configured to expand within the interior volume of the second braid and fill at least a portion of the volume.

5. The device of claim 1 wherein the first braid and the second braid are fixed relative to each other at their respective proximal regions and at least two additional locations along their lengths.

6. The device of claim 1 wherein
   the distal region of the first braid has a free distal terminus; and
   the distal region of the second braid has a distal terminus, wherein the distal terminus of the second braid is coupled to a portion of the first braid.

7. The device of claim 1 wherein the distal region of the first braid is coupled to the distal region of the second braid.

8. The device of claim 1 wherein a distal terminus of the first braid is coupled to a distal terminus of the second braid.

9. The device of claim 1, further comprising a third braid having a proximal region fixed at the proximal portion of the implant and a distal region opposite the proximal region along the length of the third braid.

10. The device of claim 1 wherein, when the implant is in an expanded configuration, both the first braid and the second braid are configured to form a first three-dimensional structure and a second three-dimensional structure, respectively, and wherein a surface area of an outer surface of the first three-dimensional structure is greater than a surface area of an outer surface of the second three-dimensional structure.

* * * * *